US009138474B2

(12) United States Patent
Kim et al.

(10) Patent No.: US 9,138,474 B2
(45) Date of Patent: Sep. 22, 2015

(54) COMPOSITION COMPRISING EXPRESSION OR ACTIVITY INHIBITORS OF NINJURIN1 FOR THE PREVENTION AND TREATMENT OF INFLAMMATORY DISEASE

(71) Applicant: SNU R&DB FOUNDATION, Seoul (KR)

(72) Inventors: Kyu-Won Kim, Seoul (KR); Hyo-Jong Lee, Seoul (KR); Bum Ju Ahn, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 1 day.

(21) Appl. No.: 14/046,436

(22) Filed: Oct. 4, 2013

(65) Prior Publication Data

US 2014/0037640 A1 Feb. 6, 2014

Related U.S. Application Data

(60) Division of application No. 13/162,226, filed on Jun. 16, 2011, now Pat. No. 8,618,072, and a continuation-in-part of application No. 12/999,005, filed as application No. PCT/KR2008/007629 on Dec. 24, 2008, now abandoned.

(30) Foreign Application Priority Data

Dec. 9, 2008 (KR) .......................... 10-2008-0124555

(51) Int. Cl.
| | |
|---|---|
| *A61K 39/00* | (2006.01) |
| *A61K 39/395* | (2006.01) |
| *A61K 31/00* | (2006.01) |
| *A61K 31/713* | (2006.01) |
| *A61K 38/17* | (2006.01) |
| *C07K 14/705* | (2006.01) |
| *C07K 16/28* | (2006.01) |
| *C12N 15/113* | (2010.01) |
| *G01N 33/50* | (2006.01) |
| *A61K 38/02* | (2006.01) |
| *C12Q 1/68* | (2006.01) |

(52) U.S. Cl.
CPC ............. *A61K 39/3955* (2013.01); *A61K 31/00* (2013.01); *A61K 31/713* (2013.01); *A61K 38/02* (2013.01); *A61K 38/1709* (2013.01); *C07K 14/705* (2013.01); *C07K 16/28* (2013.01); *C12N 15/1138* (2013.01); *G01N 33/5023* (2013.01); *C07K 2317/76* (2013.01); *C12N 2310/14* (2013.01); *G01N 2800/102* (2013.01); *G01N 2800/205* (2013.01); *G01N 2800/285* (2013.01); *G01N 2800/323* (2013.01)

(58) Field of Classification Search
None
See application file for complete search history.

(56) References Cited

U.S. PATENT DOCUMENTS

| 6,140,177 | A | 10/2000 | Schafer et al. | |
|---|---|---|---|---|
| 6,559,288 | B1 | 5/2003 | Milbrandt et al. | |
| 7,244,571 | B2 | 7/2007 | Hakonarson et al. | |
| 8,703,711 | B2 * | 4/2014 | Prat et al. ..................... | 514/17.9 |
| 2010/0310568 | A1 | 12/2010 | Prat et al. | |

FOREIGN PATENT DOCUMENTS

KR 10-2002-0003468 A 1/2002

OTHER PUBLICATIONS

Igal Ifergan, et al. "Role of Ninjurin-1 in the Migration of Myeloid Cells to Central Nervous System Inflammatory Lesions," Annals of Neurology, vol. 70, No. 5, pp. 751-763, Nov. 1, 2011. XP55027992, ISSN: 0364-5134.
Takashi Toyama, et al., "Ninjurin1 Increases p21 Expression and Induces Cellular Senescence in Human Hepatoma Cells," Journal of Hepatology, vol. 41, No. 4, pp. 637-643, Oct. 1, 2004. XP004586584, ISSN: 0168-8278.
Koike Manabu, et al. "Characterization of Ninjurin and TSC22 Induction After X-Irradiation of Normal Human Skin Cells", The Journal of Dermatology, vol. 35, No. 1, pp. 6-17, Jan. 1, 2008. XP55027987, ISSN: 0385-2407.
Kim, K., et al., "Role of Nijurin1 in the regression of hyaloid vasculature", Symposium of the Korean Society of Cardiology Basic Science Research, Jul. 2008, session 1, p. 2.
Araki, T., et al., "Mechanism of homophilic binding mediated by Ninjurin, a novel widely expressed adhesion molecule", J. Biol Chem, 1997, vol. 272, No. 34, pp. 21373-21380.
Araki, T., et al., "Ninjurin, a novel adhesion molecule, is induced by nerve injury and promotes axonal growth", Neuron, 1996, vol. 17, pp. 353-361.
International Search Report PCT/KR2008/007629 dated Aug. 27, 2009.

* cited by examiner

Primary Examiner — Sean McGarry
(74) Attorney, Agent, or Firm — Lucas & Mercanti, LLP

(57) ABSTRACT

The present invention relates to a composition comprising a Ninjurin1 expression or activity inhibitor for the prevention and treatment of inflammatory disease. Ninjurin1 protein is specifically expressed in macrophages around blood vessels, increases cell-cell adhesion and cell-matrix adhesion, increases expressions of Wnt7b (Wingless-type MMTV integration site family, member 7B) and Ang2 (angiopoietin-2), but reduces expression of Ang1 to induce apoptosis of vascular endothelial cells. In addition, Ninjurin1 protein is up-regulated when inflammation is induced and induces iNOS expression as well as increased NO generation. Therefore, the Ninjurin1 protein expression or activation inhibitor can be effectively used as an active ingredient of a composition for the prevention and treatment of inflammatory disease.

3 Claims, 29 Drawing Sheets

Fig. 3
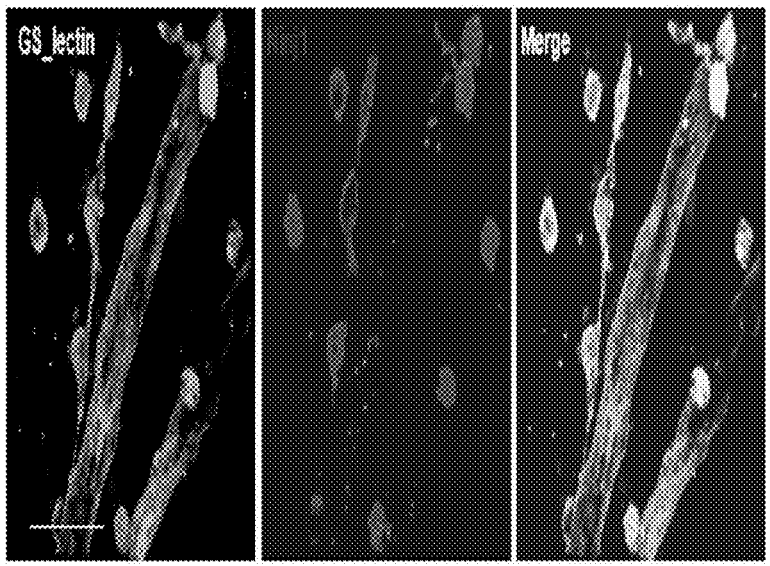
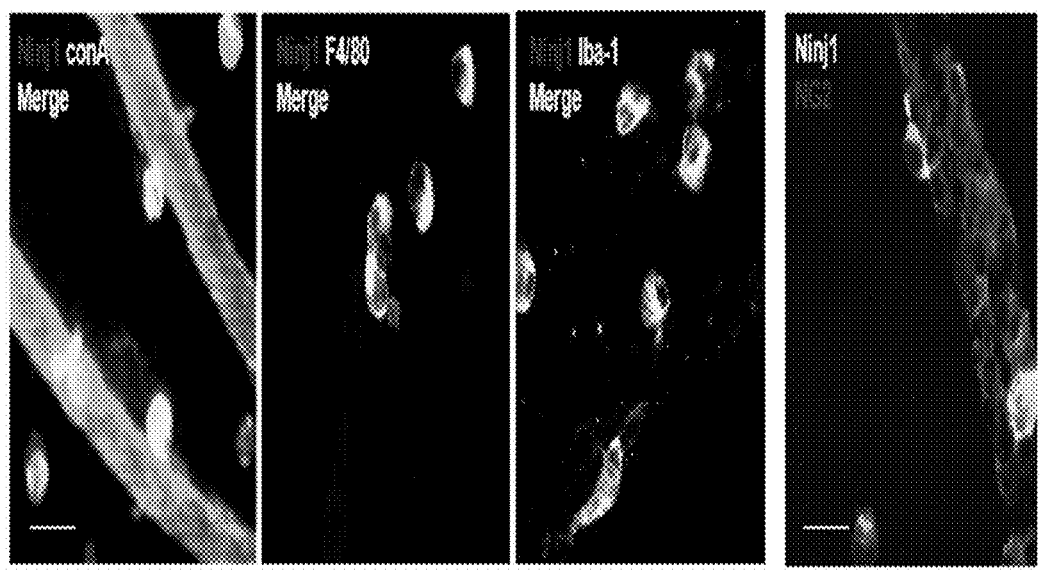

Fig. 4
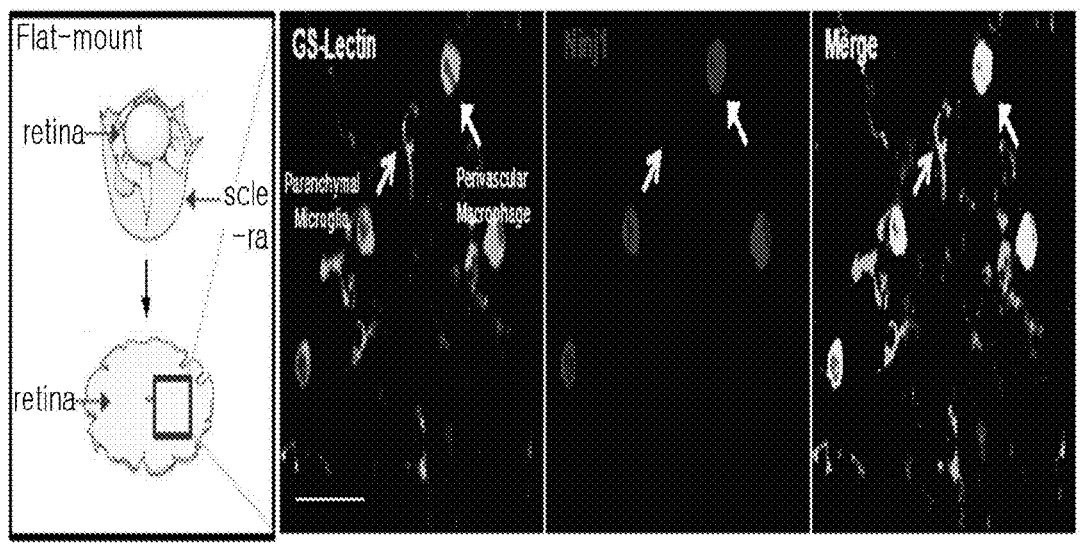
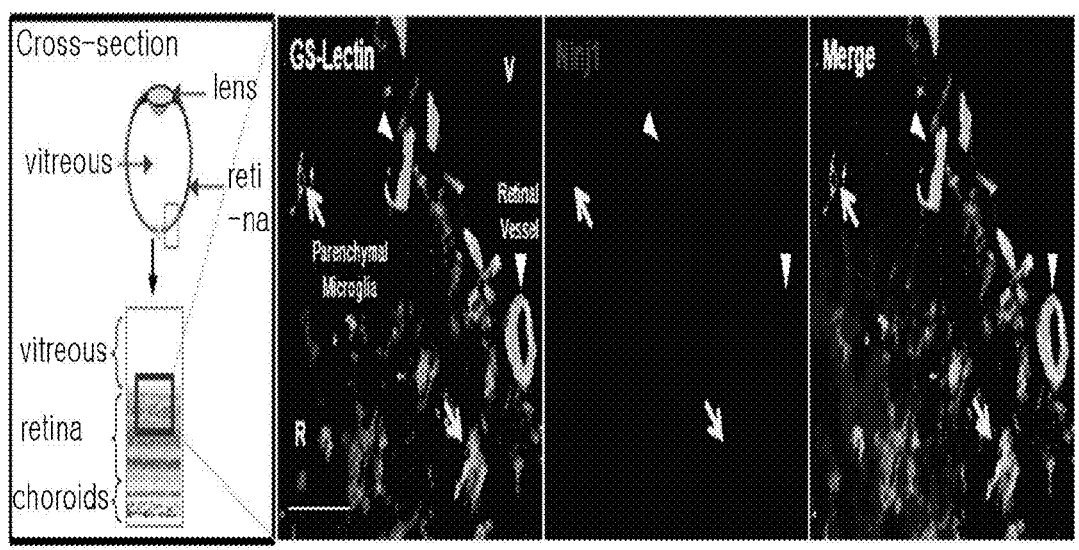

Fig. 5
a
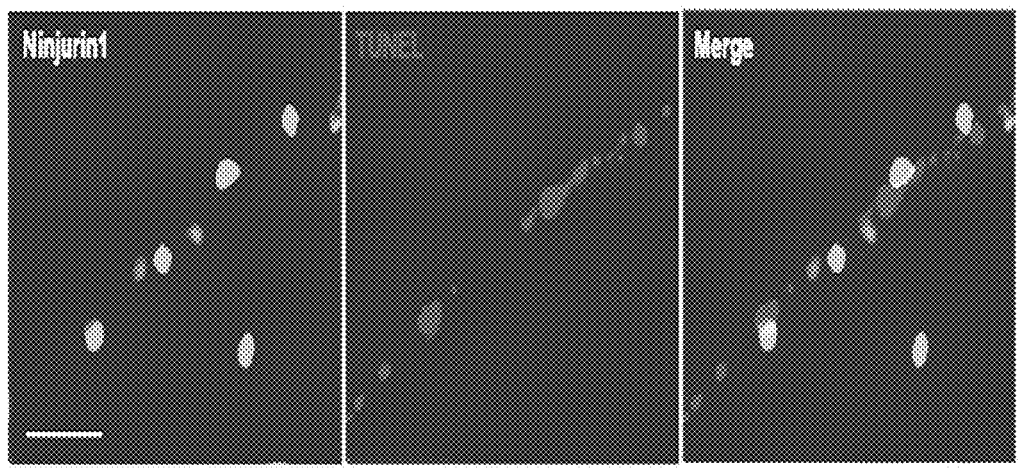
b
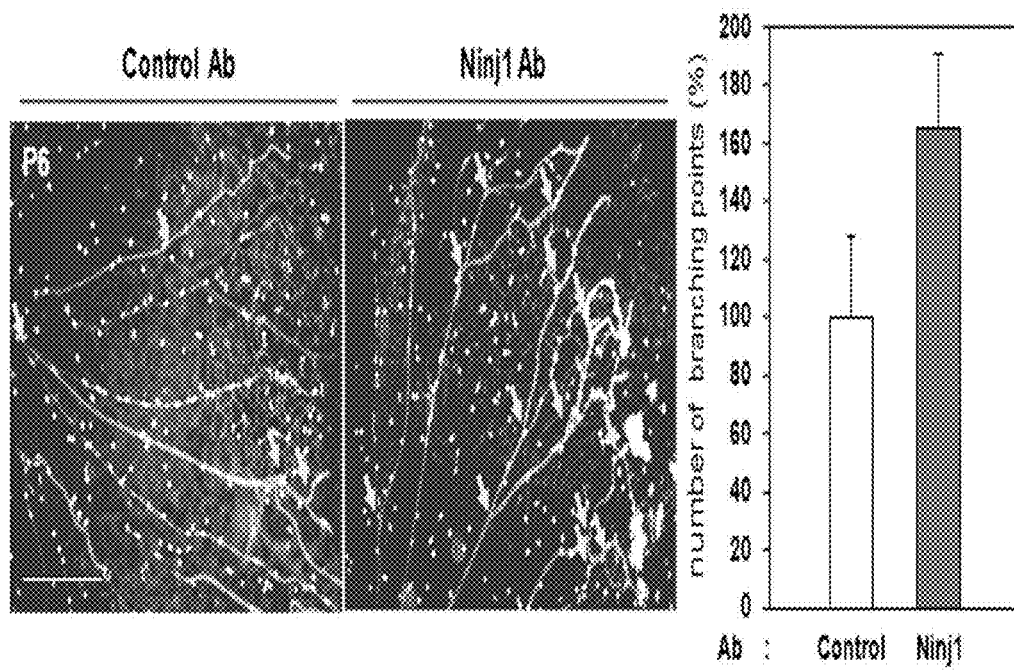

FIG. 17
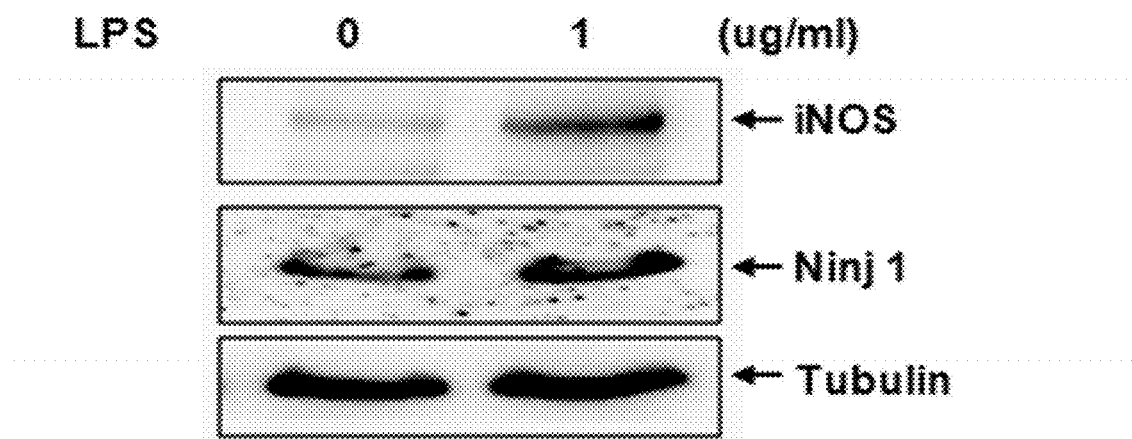
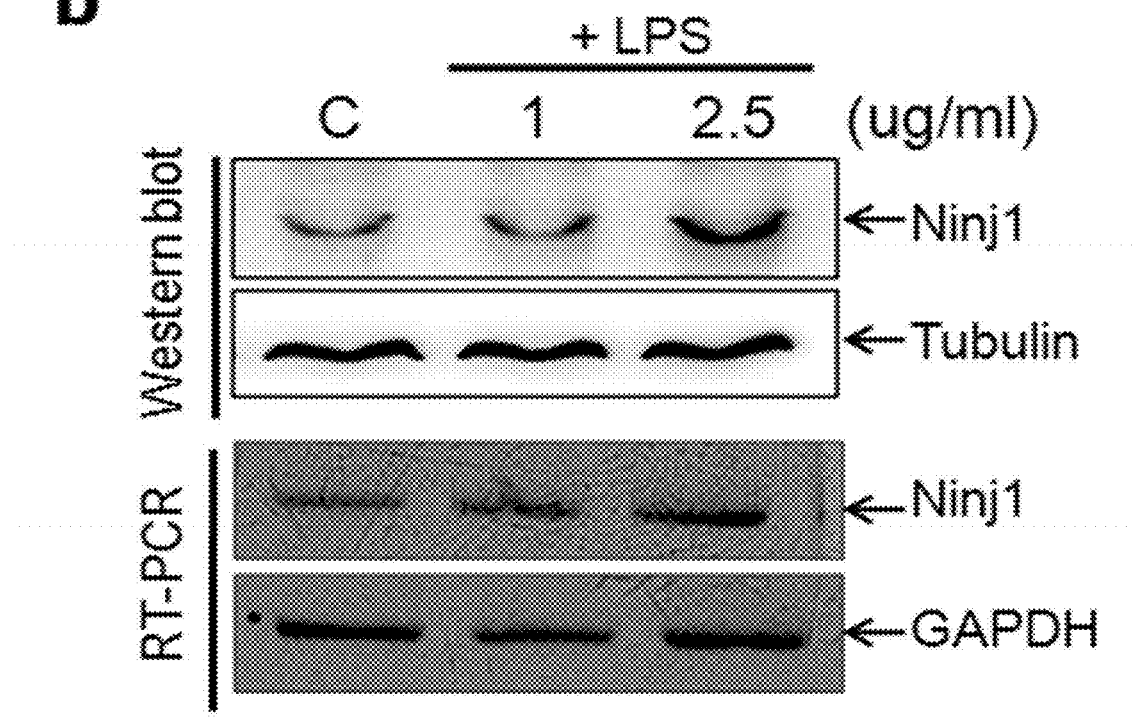

FIG. 18
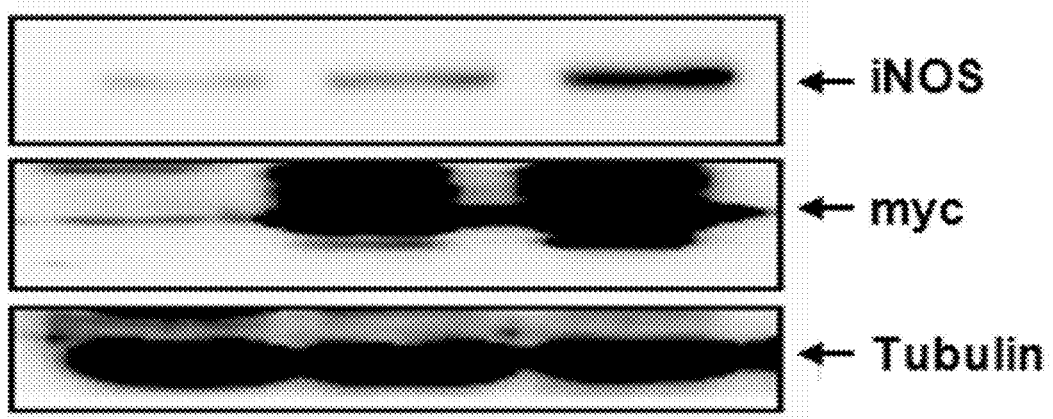
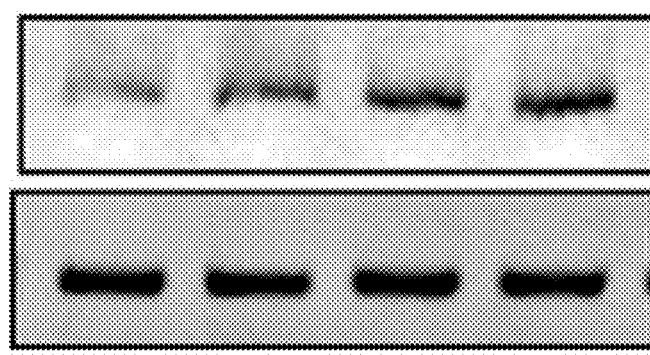

Mo ; pCS2+myc DNA

Ninj1(Myc-Ninj1) ; pCS2+myc-Ninj1 DNA

FIG. 24
a
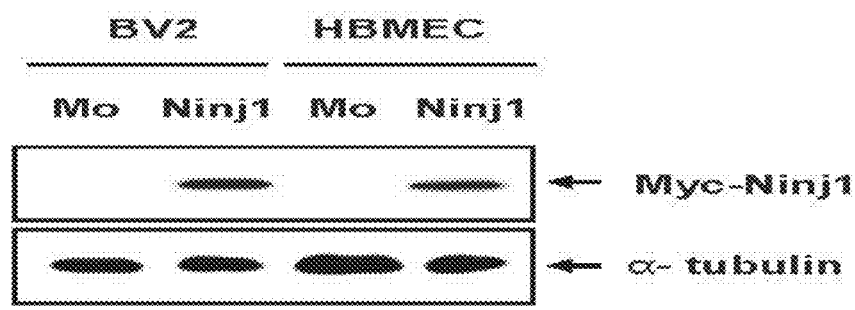
b
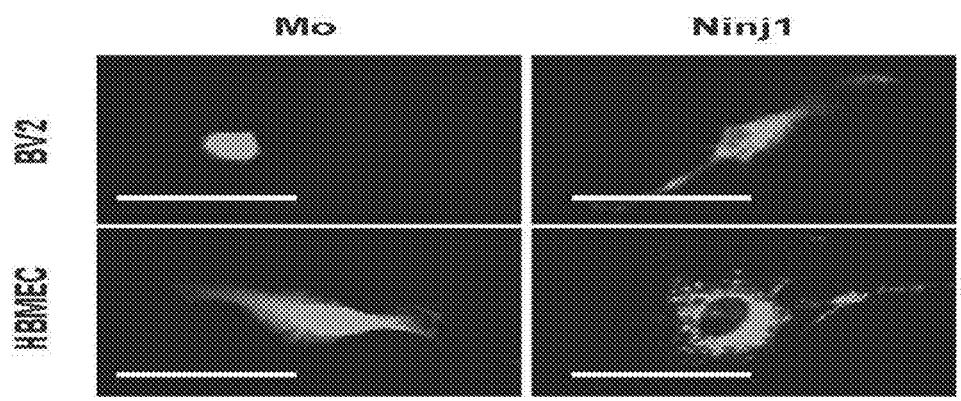

FIG. 26
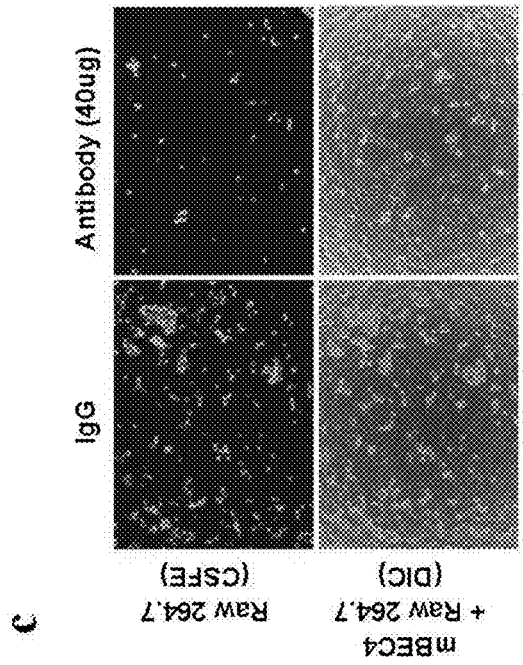
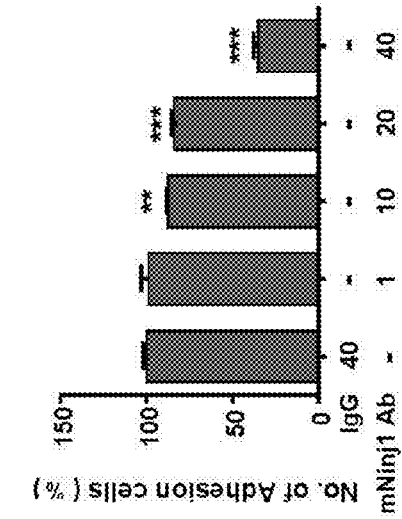
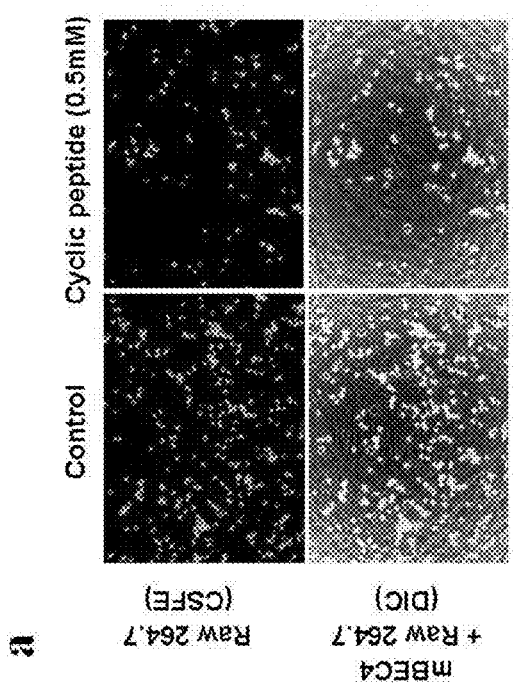
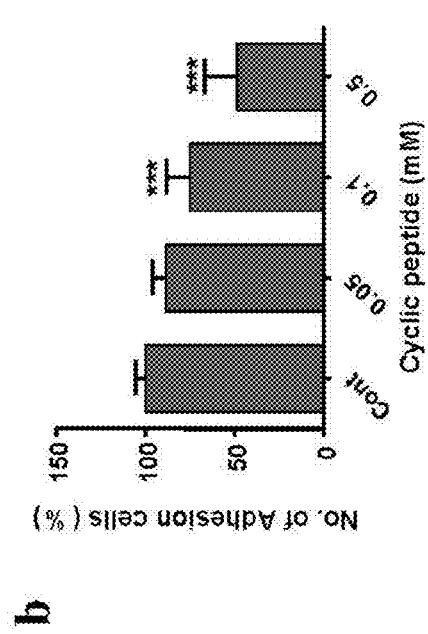

COMPOSITION COMPRISING EXPRESSION OR ACTIVITY INHIBITORS OF NINJURIN1 FOR THE PREVENTION AND TREATMENT OF INFLAMMATORY DISEASE

CROSS-REFERENCE TO RELATED APPLICATIONS

This application is a divisional of U.S. patent application Ser. No. 13/162,226 filed Jun. 16, 2011, which is a continuation-in-part of U.S. patent application Ser. No. 12/999,005 filed Dec. 10, 2010, which in turn claims the benefit of Korean Application No. 10-2008-0124555 filed Dec. 9, 2008, through PCT/KR2008/007629 filed Dec. 24, 2008, the contents of each of which are incorporated herein by reference.

TECHNICAL FIELD

The present invention relates to a composition comprising a Ninjurin1 expression or activity inhibitor for the prevention and treatment of inflammatory disease. Particularly, Ninjurin1 protein specifically expressed in macrophages around blood vessels interacts with vascular endothelial cells to induce apoptosis of the cells via Wnt7b-Ang signal transduction pathway, increases iNOS expression and promotes NO generation to induce inflammation at last. And the present invention relates to a composition comprising such a Ninjurin1 expression or activity inhibitor as an active ingredient for the prevention and treatment of inflammatory disease.

BACKGROUND OF INVENTION

Ninjurin1 was first reported by Toshiyuki Araki et al in 1996 (Araki, T. & Milbrandt, J., Neuron 17, 353-361, 1996). It was found during the screening of a gene up-regulated in Schwann cells after damage caused by transection or crush in sciatic nerve.

Phylogenetic tree was made with proteins having homology with Ninjurin based on protein information in GeneBank (Zhang, S. et al., Genes & development 20, 1899-1910, 2006). It was reported that vertebrate have two Ninjurin proteins, Ninjurin1 and Ninjurin2. In fact, Ninjurin1 and Ninjurin2 were found in vertebrate such as human, mouse and rat. Ninjurin identified in invertebrate is classified into three types, A, B, and C, and specifically identified in drosophila, mosquito, and so on. Human Ninjurin1 shows 90% homology with mouse Ninjurin1 (Chadwick, B. P. et al., Genomics 47, 58-63, 1998). In the meantime, human Ninjurin1 shows 55% homology with human Ninjurin2 (Araki, T. & Milbrandt, J., J Neurosci 20, 187-195, 2000).

Human Ninjurin1 is located at chromosome 9q22 and is composed of 152 amino acids. Mouse Ninjurin1, in the meantime, is located at chromosome 13 and is composed of 152 amino acids. Two transmembrane domains are predicted in the amino acid sequence of Ninjurin1. It was also confirmed by experiments that Ninjurin1 is the protein located in cell membrane (Araki, T. & Milbrandt, J., Neuron 17, 353-361, 1996). Accordingly, it can be predicted that N-terminal region of Ninjurin1 is stretched long out of cell.

Ninjurin1 is expressed in diverse tissues. For example, it is expressed at RNA level in the heart, brain, placenta, lung, liver, SK. Muscle, kidney, pancreas, spleen, thymus, prostate, testis, ovary, small int., colon, blood, adrenal gland and dorsal root ganglia (DRG). It is expressed at protein level in the liver, kidney, thymus, uterus, adrenal gland, retina and dorsal root ganglia (Araki, T. et al., The Journal of biological chemistry 272, 21373-21380, 1997).

The functions of Ninjurin1 known so far are in relation to 1) cell adhesion, 2) neurite outgrowth, 3) cellular senescence, and 4) cancer.

Particularly, regarding the function of Ninjurin1 in relation to cell adhesion 1), it was reported via cell aggregation experiment performed with Jurkat T cell leukemia that Ninjurin1 increased aggregation among cells (Araki, T. & Milbrandt, J., Neuron 17, 353-361, 1996). For the cell adhesion, polymerization of actin filaments, oxidative phosphorylation, divalent cation and proper pH (pH 7-11) are required (Araki, T. et al., The Journal of biological chemistry 272, 21373-21380, 1997). In the study using drosophila, Ninjurin A protein digested with MMP1 (matrix metalloproteinase 1) acted as a signal molecule to inhibit cell adhesion (Zhang, S. et al., Genes & development 20, 1899-1910, 2006).

To investigate the function of Ninjurin1 in relation to neurite outgrowth 2), CHO cells were monolayer-cultured, on which DRG neurite cells were cultured. When CHO cells over-expressing Ninjurin1 were used, neurite cell proliferation was increased (Araki, T. & Milbrandt, J., Neuron 17, 353-361, 1996). When the amino acid sequence ranging from the $26^{th}$ to the $37^{th}$ residue of Ninjurin1 protein was modified, neurite cell proliferation was inhibited (Zhang, S. et al., Genes & development 20, 1899-1910, 2006). When DRG neurite cells and skin-derived fibroblast-like cells (FLCs) were co-cultured, when Ninjurin1 was expressed, neurite cells were being proliferated but when Ninjurin1 was inhibited by an antibody not to be functioning, neurite cell proliferation was inhibited (Jerregard, H. et al., Journal of neurocytology 30, 327-336, 2001).

Regarding cellular senescence 3), when Ninjurin1 was over-expressed, cell cycle was arrested in G1 stage after $p21^{WAF1/Cip1}$ transcription, resulting in a significant inhibition of cell proliferation. Besides, when Ninjurin1 was over-expressed, senescence-associated β-galactosidase activity and autofluorescence pigment were increased. Ninjurin1 is also up-regulated in hepatocellular carcinoma tissue, suggesting that Ninjurin1 might be involved in cellular senescence which is the target of anti-cancer treatment (Toyama, T. et al., Journal of hepatology 41, 637-643, 2004).

In studies of Ninjurin1 in relation to cancer 4), Ninjurin1 was confirmed to be up-regulated in hepatocellular carcinoma including virus infection in the liver or cirrhosis (Kim, J. W. et al., Molecules and cells 11, 151-157, 2001). Ninjurin1 was also increased in acute lymphocytic leukemia. Ninjurin1 was directly increased during the screening of a gene regulated by the tumor suppressing protein p53 using microarray (Kannan, K. et al., Oncogene 20, 2225-2234, 2001).

However, it has not been disclosed yet whether Ninjurin1 is involved in the functions of macrophages, vascular decrease and inflammation induction.

So, the present inventors have been studied on the involvement and mechanism of Ninjurin1 in relation to macrophages, during which the inventors confirmed that Ninjurin1 was expressed specifically in macrophages around blood vessels, increased cell-matrix and cell-cell adhesion, increased Wnt7b (Wingless-type MMTV integration site family, member 7B) and Ang2 (angiopoietin-2) expressions, and accelerated apoptosis of vascular endothelial cells (VECs) by reducing Ang1 (angiopoietin-1) expression. Further, the present inventors completed this invention by confirming that Ninjurin1 was up-regulated when inflammation was induced by LPS in vivo and in vitro and increased iNOS expression and NO generation and accordingly confirming that Ninjurin1 increased the activity of macrophages to induce inflammation.

SUMMARY OF THE INVENTION

Technical Problem

It is an object of the present invention to provide a method for preventing and treating inflammatory disease caused by over-activation of macrophages containing the step of inhibiting the expression or activity of Ninjurin1 protein.

Technical Solution

To achieve the above object, the present invention provides a composition comprising a Ninjurin1 protein expression or activity inhibitor for the prevention and treatment of inflammatory disease.

The present invention also provides a method for treating inflammatory disease containing the step of administering a pharmaceutically effective dose of the said composition to a subject with inflammatory disease.

The present invention also provides a method for preventing inflammatory disease containing the step of administering a pharmaceutically effective dose of the said composition to a subject.

The present invention also provides a use of a Ninjurin1 expression or activity inhibitor for the preparation of a composition for the prevention and treatment of inflammatory disease.

In addition, the present invention provides a screening method of a preventive and therapeutic agent for inflammatory disease comprising the following steps:

1) treating samples to a cell line expressing Ninjurin1 protein;
2) measuring the expression of Ninjurin1 protein in the cell line; and
3) selecting a sample that inhibited the expression of Ninjurin1 protein, compared with the expression level in the control.

BRIEF DESCRIPTION OF DRAWINGS

The application of the preferred embodiments of the present invention is best understood with reference to the accompanying drawings, wherein:

FIG. 3 is a set of diagrams illustrating the location of Ninjurin1 expression around blood vessels in the mouse oculus: (a) diagram illustrating GS-lectin (green) and Ninjurin1 (red) (if overlapped: yellow) in the oculus of the mouse at 5 days (P5), observed under fluorescent microscope after double immunostaining; (b) diagram illustrating Ninjurin1 (red) and ConA (green) (if overlapped: yellow), Ninjurin1 (red) and F4/80 (green) (if overlapped: yellow), and Ninjurin1 (red) and Iba-1 (green) (if overlapped: yellow) in the oculus, observed under fluorescent microscope after double immunostaining; and (c) diagram illustrating Ninjurin1 (green) and NG2 (red) (if overlapped: yellow) in the oculus, observed under fluorescent microscope after double immunostaining FIG. 4 is a set of diagrams illustrating the location of Ninjurin1 expression and macrophages around blood vessels in the mouse oculus: (a) diagram illustrating Ninjurin1 (red) and GS-lectin (green) in the oculus of the mouse at 5 days (P5), observed under fluorescent microscope after double immunostaining. At this time, hyaloid vessels were eliminated from the oculus using 5% gelatin. (b) diagram illustrating Ninjurin1 (red) and parenchymal microglia (green) in the retina, observed under fluorescent microscope after double immunostaining (white arrow: retinal vessel; yellow arrow: parenchymal microglia stretching its arm).

FIG. 5 is a set of diagrams illustrating the changes of vascular endothelial cells over Ninjurin1 expression in the mouse vitreous; (a) diagram illustrating that macrophages expressing Ninjurin1 in vitreous of the mouse at 8 days (P8) were adhered to vascular endothelial cells being through apoptosis, which was observed under immunofluorescent microscope; and (b) diagram illustrating that vitreous of the mouse at 6 days (P6) neutralized with Ninjurin1 antibody was stained with GS-lectin (green), followed by observation under fluorescent microscope (yellow arrow: branching point of blood vessel).

FIG. 17 is a set of diagrams illustrating the Ninjurin1 expression and iNOS expression, the index of inflammation, in BV2 cells treated with LPS: (a) diagram illustrating the iNOS expression examined by Western blotting with BV2 cells treated with different concentrations of LPS; and (b) diagram illustrating the Ninjurin1 expression examined by RT-PCR and Western blotting with BV2 cells treated with different concentrations of LPS.

FIG. 18 is a set of diagrams illustrating the iNOS expression over Ninjurin1 expression: (a) diagram illustrating the result of Western blotting examining iNOS expressions in BV2 cells expressing Myc-mock and BV2 cells expressing Myc-Ninjurin1; and (b) diagram illustrating the result of RT-PCR examining iNOS expressions in BV2 cells expressing Myc-mock and BV2 cells expressing Myc-Ninjurin1.

FIG. 26 shows that peptide (a, b) and antibody (c, d) significantly reduced Ninjurin1-mediated adhesion activity between leukocyte and endothelial cells.

DETAILED DESCRIPTION OF THE INVENTION

Figure 1:
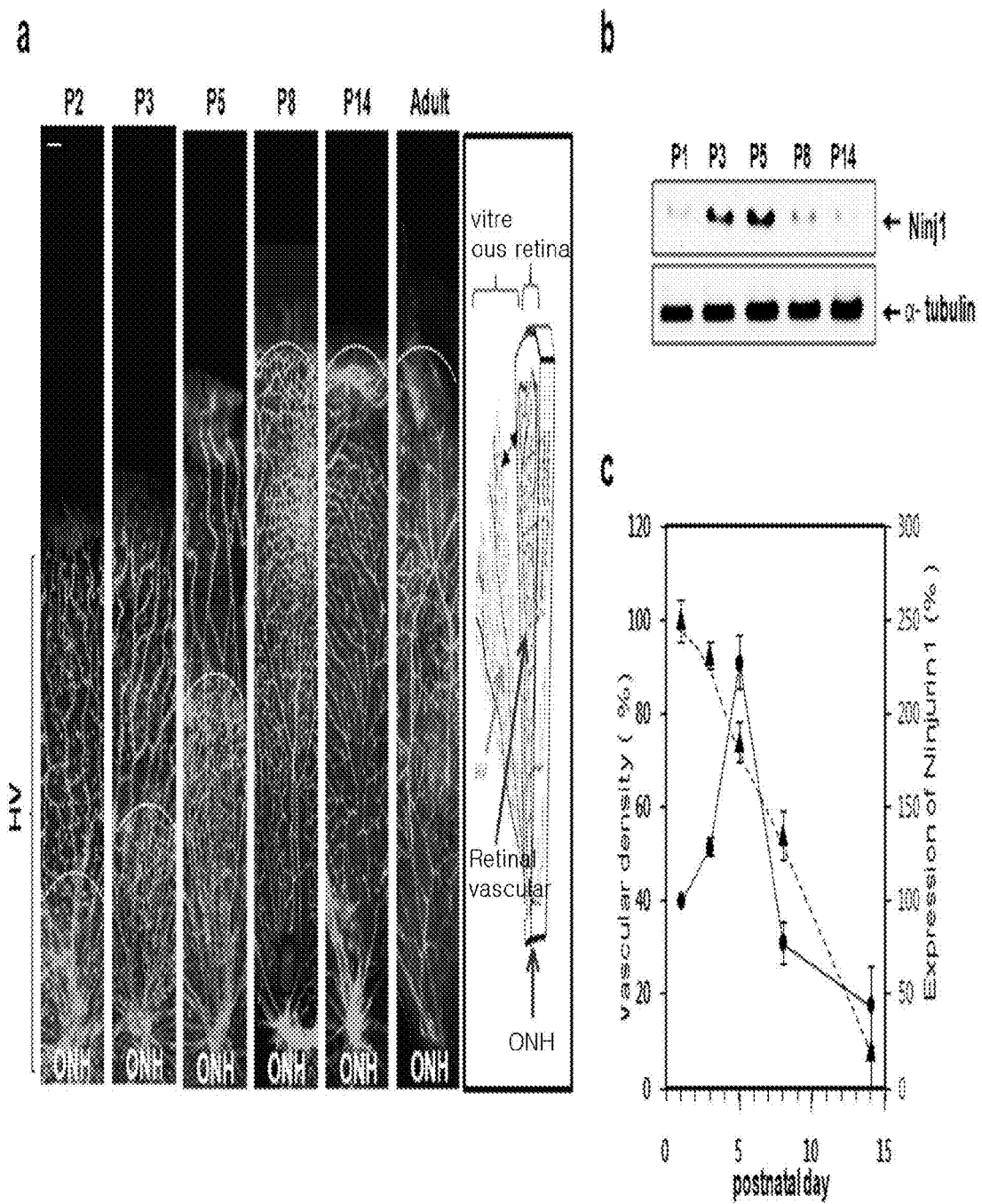
FIG. 1 is a set of diagrams illustrating the ocular development stage of a mouse and Ninjurin1 expression over the time: (a) vitreous and incipient retinal vessel stained with GS-lectin (green) of mice at 2 days (P2), at 3 days (P3), at 5 days (P5), at 8 days (P8), and at 14 days (P14) from birth and an adult mouse; (b) graph illustrating Ninjurin1 protein expression in oculus of those mice examined by Western blotting; (c) graph illustrating blood vessel density (▲) and Ninjurin1 expression (●) over the ocular development in those mice (considering the value at P1 as 100%).

The present invention provides a composition comprising a Ninjurin1 protein expression or activity inhibitor for the prevention and treatment of inflammatory disease.

The said Ninjurin1 protein preferably has the amino acid sequence represented by SEQ. ID. NO: 1, but not always limited thereto.

The Ninjurin1 protein expression inhibitor is preferably selected from the group consisting of an antisense nucleotide complementarily binding to Ninjurin1 mRNA, short interfering RNA and short hairpin RNA, but not always limited thereto.

The Ninjurin1 protein activity inhibitor is preferably selected from the group consisting of a compound complementarily binding to Ninjurin1 protein, a peptide, a peptide mimetix and an antibody, but not always limited thereto.

The inflammatory disease herein is preferably selected from the group consisting of rheumatic arthritis, inflammatory bowel disease, ankylosing spondylitis, psoriasis, atherosclerosis and multiple sclerosis, but not always limited thereto and any inflammatory disease caused by over-activation of macrophages can be included.

In this invention, to investigate the relation of Ninjurin1 with macrophages, mice at different days after birth were prepared and Ninjurin1 protein expression and location where Ninjurin1 protein was expressed particularly in oculus were investigated under immunofluorescece microscope and by Western blotting during ocular development stage. As a result, Ninjurin1 was largely expressed in the early ocular development stage and specifically in macrophages around blood vessels (see FIGS. 1-4). The above result indicates that Ninjurin1 is expressed specifically in macrophages and is involved in the interaction of macrophages with blood vessel cells.

In this invention, to investigate the effect of Ninjurin1 on vascular endothelial cells, oculus was extracted respectively from a mouse at some days after birth and a mouse where Ninjurin was neutralized by a Ninjurin1 antibody. Then, the locations and amounts of macrophages and vascular endothelial cells in the oculus were observed under immunofluorescece microscope. As a result, macrophages expressing Ninjurin1 were adhered on vascular endothelial cells which were being through apoptosis, and the level of vitreous vascular endothelial cells in the mouse neutralized by a Ninjurin1 antibody was higher than that in the control (see FIGS. 5 and 6). The above results indicate that macrophages expressing Ninjurin1 are involved in apoptosis of vitreous vascular endothelial cells.

In this invention, to investigate the effect of Ninjurin1 on cell-cell adhesion and cell-matrix adhesion, cells transformed or not transformed with Ninjurin1 were used for the experiment examining cell adhesion to different matrixes and coagulation. As a result, over-expression of Ninjurin1 increased macrophage-vascular endothelial cell adhesion and also increased macrophage binding to such matrixes as collagen, fibronectin and vitronectin, and at the same time increased coagulation near blood vessel cells (see FIGS. 7 and 8). Therefore, it was confirmed that Ninjurin1 was involved in cell-cell adhesion and cell-matrix adhesion.

In this invention, to investigate the effect of Ninjurin1 on Wnt-Ang signal transduction system, expression patterns of Wnt7b, p38, MAPK (p44/p42), JNK (p54/46), Ang1 and Ang2 over the Ninjurin1 expression patterns were investigated in Ninjurin1 over-expressing cells and in Ninjurin1 expression inhibited cells by RT-PCR and real-time PCR. As a result, when Ninjurin1 expression was increased, expressions of Wnt7b, phosphorylated p38, MAPK (p44/p42) and JNK (p54/46) were also increased (see FIG. 9-FIG. 13). To investigate the relation of Ninjurin1 and Wnt7b with Ang1 and Ang2, intracellular concentrations of Wnt7b and Ninjurin1 were investigated in the presence of different concentrations of Ang1 or Ang2. As a result, Wnt7b was down-regulated as Ang1 concentration was increased, while Wnt7b was up-regulated as Ang2 concentration was increased (see FIG. 14). To investigate the effect of Ninjurin1 on apoptosis mediated by Ang2, pericytes were treated with the cell culture solution in which Ninjurin1 was over-expressed in the presence of Ang2, followed by examining digestion by caspase 3 and apoptosis. As a result, over-expression of Ninjurin1 increased digestion by caspase3 and apoptosis (see FIG. 15). In conclusion, Ninjurin1 increased the expressions of Wnt7b and Ang2 but reduced the expression of Ang1, suggesting that Ninjurin1 induced apoptosis of vitreous vascular endothelial cells by regulating Wnt-Ang signal transduction system.

That is, Ninjurin1 is specifically expressed in macrophages around blood vessels, so that it mediates direct interaction between macrophages and vascular endothelial cells and thereby activates Wnt-Ang pathway, resulting in the induction of apoptosis and decrease of blood vessels. Therefore, apoptosis in blood vessel cells can be inhibited by suppressing expression or activation of Ninjurin1.

In this invention, to investigate Ninjurin1's involvement in inflammation reaction, lipopolysaccharide (LPS) was intraperitoneally injected into a rat to induce inflammation. Then, oculus was extracted, followed by observation by immunofluorescence staining. As a result, LPS administration increased the number of macrophages expressing Ninjurin1 (see FIG. 16).

In this invention, cells were treated with LPS to induce inflammation. Then, Ninjurin1 expression and iNOS expression, the index of inflammation, were investigated and also iNOS expression patterns varying from Ninjurin1 expression and generation of nitric oxide (NO), the inflammatory mediator, were measured. As a result, as LPS concentration was increased, Ninjurin1 expression was also increased. And as Ninjurin1 expression was increased, iNOS expression and NO generation were increased (see FIG. 17-FIG. 20). In conclusion, Ninjurin1 was up-regulated when inflammation was induced and the increase of Ninjurin expression resulted in the increase of iNOS expression and NO generation, suggesting that Ninjurin1 is involved in inflammation inducing mechanism.

That is, Ninjurin1 increases iNOS and NO levels to induce inflammation. So, inflammation can be inhibited by suppressing Ninjurin1 expression or activation.

As explained hereinbefore, Ninjurin1 increases the activity of macrophages, and over-activation of macrophages causes diverse diseases including rheumatic arthritis, inflammatory bowel disease, ankylosing spondylitis, psoriasis (Morand, E. F. et al., *Intern Med J* 35, 419-426, 2005), atherosclerosis (Choudhury, R. P., et al., *Nat Clin Pract Cardiovasc Med* 2, 309-315, 2005), and multiple sclerosis (Minagar, A. et al., *J Neurol Sci* 202, 13-23, 2002), etc. Therefore, such diseases, particularly inflammatory disease caused by over-activation of macrophages can be prevented and treated by inhibiting Ninjurin1 expression or activation.

The composition for the prevention and treatment of inflammatory disease comprising a Ninjurin1 protein expression or activation inhibitor as an active ingredient can include the said active ingredient by 0.0001-50 weight % by the total weight of the composition.

The composition of the present invention can include one or more effective ingredients having the same or similar function to the Ninjurin1 protein expression or activation inhibitor.

The composition of the present invention can include one or more pharmaceutically acceptable carriers such as saline, sterilized water, Ringer's solution, buffered saline, dextrose solution, maltodextrin solution, glycerol, ethanol, liposome and a mixture comprising one or more of those components in addition to the said active ingredient. If necessary, a general additive such as an antioxidant and buffer can be additionally added. The composition of the present invention can be formulated in different forms including aqueous solutions, suspensions and emulsions for injection, pills, capsules, granules or tablets by mixing with diluents, dispersing agents, surfactants, binders and lubricants. A target organ specific antibody or other ligands can be mixed with one of the said carriers to be delivered to the target organ. The composition can further be prepared in suitable forms according to ingredients by following the method represented in Remington's Pharmaceutical Science (the newest edition), Mack Publishing Company, Easton Pa.

Nucleotide or nucleic acid used in this invention can be formulated for oral, local, parenteral, intranasal, intravenous, intramuscular, hypodermic, ophthalmic or transdermal administration. It is more preferred to prepare nucleic acid or vector as an injectable formulation. For direct injection, the injectable composition can be mixed with a pharmaceutically acceptable carrier. The composition of the present invention can also include a freeze-dried composition facilitating injection using sterilized isotonic solution or distilled water or saline. Direct injection of nucleic acid into a tumor of a patient brings the effect of focusing the treatment effect on infected tissues, which favors the treatment. Dosage of the nucleic acid can be regulated according to diverse parameters, particularly a gene or a vector, administration method, target disease and required treatment period, etc. in addition, weight, age, gender, health condition, administration times, administration method, excretion and severity of a disease. The preferable dosage is 0.0001~100 mg/kg per day and more preferably 0.001~10 mg/kg per day, and administration frequency is once a day or preferably a few times a day.

The present invention also provides a method for treating inflammatory disease containing the step of administering a pharmaceutically effective dose of the said composition to a subject with inflammatory disease.

The present invention also provides a method for preventing inflammatory disease containing the step of administering a pharmaceutically effective dose of the said composition to a subject.

The inflammatory disease herein is preferably selected from the group consisting of rheumatic arthritis, inflammatory bowel disease, ankylosing spondylitis, psoriasis, atherosclerosis and multiple sclerosis, but not always limited thereto and any inflammatory disease caused by over-activation of macrophages can be included.

The composition of the present invention can include one or more effective ingredients having the same or similar function to the Ninjurin1 protein expression or activation inhibitor.

The composition of the present invention can be administered orally or parenterally and be used in general forms of pharmaceutical formulation.

The composition of the present invention can be prepared for oral or parenteral administration by mixing with generally used diluents or excipients such as fillers, extenders, binders, wetting agents, disintegrating agents and surfactant. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The effective dosage of the composition can be determined according to weight, age, gender, health condition, diet, administration frequency, administration method, excretion and severity of a disease. The preferable dosage is 0.0001~100 mg/kg per day and more preferably 0.001~10 mg/kg per day, and administration frequency is once a day or preferably a few times a day.

The composition of the present invention can be administered alone or treated together with surgical operation, hormone therapy, chemo-therapy and biological regulators.

The present invention also provides a use of a Ninjurin1 expression or activity inhibitor for the preparation of a composition for the prevention and treatment of inflammatory disease.

The said Ninjurin1 protein preferably has the amino acid sequence represented by SEQ. ID. NO: 1, but not always limited thereto.

The Ninjurin1 protein expression inhibitor is preferably selected from the group consisting of an antisense nucleotide complementarily binding to Ninjurin1 mRNA, short interfering RNA and short hairpin RNA, but not always limited thereto.

The Ninjurin1 protein activity inhibitor is preferably selected from the group consisting of a compound complementarily binding to Ninjurin1 protein, a peptide, a peptide mimetix and an antibody, but not always limited thereto.

The inflammatory disease herein is preferably selected from the group consisting of rheumatic arthritis, inflammatory bowel disease, ankylosing spondylitis, psoriasis, atherosclerosis and multiple sclerosis, but not always limited thereto and any inflammatory disease caused by over-activation of macrophages can be included.

Ninjurin1 protein of the present invention is expressed specifically in macrophages around blood vessels, increases cell-cell adhesion and cell-matrix adhesion, increases the expressions of Wnt7b and Ang2, reduces Ang1 expression and accelerates apoptosis of vascular endothelial cells. Ninjurin1 protein is up-regulated when inflammation is induced, and then it increases iNOS expression and NO generation. Therefore, a Ninjurin1 protein expression or activation inhibitor can be effectively used as an active ingredient of a composition for the prevention and treatment of inflammatory disease.

In addition, the present invention provides a screening method of a preventive and therapeutic agent for inflammatory disease comprising the following steps:

1) treating samples to a cell line expressing Ninjurin1 protein;
2) measuring the expression of Ninjurin1 protein in the cell line; and
3) selecting a sample that inhibited the expression of Ninjurin1 protein, compared with the expression level in the control.

In this method, the Ninjurin1 protein of step 1) preferably has the amino acid sequence represented by SEQ. ID. NO: 1, but not always limited thereto.

In this method, the protein expression of step 2) is measured by one of the methods selected from the group consisting of immunofluorescence method, ELISA, Western blotting, and RT-PCR, but not always limited thereto.

In this method, the inflammatory disease of step 2) is preferably selected from the group consisting of rheumatic arthritis, inflammatory bowel disease, ankylosing spondylitis, psoriasis, atherosclerosis and multiple sclerosis, but not always limited thereto.

Advantageous Effect

Ninjurin1 protein of the present invention is expressed specifically in macrophages around blood vessels and then mediated direct interaction between macrophages and vascular endothelial cells. By which, it activates Wnt-Ang pathway to induce apoptosis. Ninjurin1 also increases iNOS expression and NO generation, suggesting that it is directly involved in inflammation reaction. Therefore, the said Ninjurin1 expression or activation inhibitor can be effectively used as an active ingredient of a composition for the prevention and treatment of inflammatory disease.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Test Animals and Conditions Thereof

Specific pathogen-free (SPF) pregnant Sprague-Dawley (SD) line rats and male ICR mice/SD rats were purchased from Samtaco BioKorea Co., and then maintained in an animal facility at College of Pharmacy Seoul National University under germ-free conditions during the whole experimental period. All the animal tests were approved by Institute of Laboratory Animal Resources Seoul National University (http://ilar.snu.ac.kr).

Example 2

Cell Culture and Preparation of Cell Lysate and Cell Culture Solution and Conditions Thereof Primary cultured human microvascular pericytes (Applied Cell Biology Research Institute) were cultured in Dulbecco's modified Eagle's medium (DMEM); Raw 264.7 cells (TIB-71™) and BV2 cells were cultured in DMEM; and HUVEC cells were cultured in M199 supplemented with 20% FBS (Invitrogen, Grand Island, N.Y.). Those cells were cultured at 37° C. in humid air composed of 95% $O_2$ and 5% $CO_2$. Raw cells and BV2 cells were transformed by using Lipofectamine Plus Reagent (Invitrogen). Cell lysate was prepared by using lysis buffer (40 mM Tris-Cl pH 8.4, 10 mM EDTA, 120 mM NaCl, 0.1% NP-40). To prepare culture solution to treat human microvascular pericytes, transformed macrophages were cultured in serum (FBS)-free DMEM for 24 hours, which were then filtered with 0.22 μgym filter paper (Millipore), followed by 10 fold concentration using centrifugation filtering tube (Millipore). For the chemical treatment, cells were cultured at the density of 60-70% and then treated with Ang1 and Ang2 (500-1000 ng/ml) independently or together in serum free condition for 14-16 hours. To understand signal transduction pathway, cells were transformed with Mock or Ninjurin1 cDNA. Serum was depleted for 14-16 hours and then the cells were treated with SB203580 (Sigma), the p38 inhibitor, for 24 hours.

Example 3

Construction of Ninjurin1 Protein Expression Vector

Wild-type mouse Ninjurin1 cDNA was synthesized from NIH-3T3 fibroblasts by RT-PCR. At this time, the primer represented by SEQ. ID. NO: 2 (5'-GGGAATTCCATG-GAGTCGGGCACTGAGGA-3', upstream containing EcoRI restriction enzyme site) and the primer represented by SEQ. ID. NO: 3 (5'-CTCCTCGAGTTCTACTGCCGGGGCGC-CACGT-3', downstream containing Xho I restriction enzyme site) were used. The synthesized cDNA was inserted in pCS2+ vector (labeled with Myc) to express the cDNA in mammalian cells.

Experimental Example 1

Ninjurin1 Expression Over the Time During Ocular Development

The present inventors sacrificed those mice at 2 days (P2), at 3 days (P3), at 5 days (P5), at 8 days (P8), and at 14 days (P14) and adult mice prepared in Example 1 and extracted their oculus, followed by GS-lectin immunostaining to observe vitreous and incipient retinal vessel development.

Particularly, immunostaining was performed as follows. The antibodies used herein were Ninjurin1 (1:500, provided from Dr. J. Milbrandt), VE-cadherin, GS-lectin (1:500, Santa Cruz), Iba-1 (1:500, Wako), NG2 (1:300, Chemicon) and cleaved-caspase3 (1:500, Cell Signaling). Nuclei were stained with DAPI and propidium iodide (Molecular Probes). Tissues and cells were reacted with the said primary antibody, followed by reaction with secondary antibody exemplified by Alexa488 conjugated IgG or Alexa546 conjugated IgG (Molecular Probes). Images were obtained by using Axiovert M200 microscope (Zeiss, Oberkochen, Germany), followed by analysis with NIH-image J program. Immunostaining was further performed under the same conditions.

Ninjurin1 protein expression in each oculus of mice having different days was investigated by Western blotting.

Particularly, Western blotting was performed as follows. At this time, Ninjurin1 (BD Phaminogen), c-Myc (Santa Cruz), α-tubulin (BioGenex), caspase-3 (Cell signaling), iNOS (Santa Cruz) specific primary antibodies were used. Anti-mouse/rabbit horseradish peroxidase conjugated secondary antibody was purchased from Pierce Chemical Co. Color development was performed by using ECL Plus reagent (Amersham Biosciences), followed by detection with LAS-3000 (Fujifilm). Recombinant Ang1 and Ang2 were purchased from R&D Systems INC. Ponceau S solution was purchased from Sigma. Western blotting was performed under the same conditions.

Analysis of results and statistics were performed as follows. Band strength was quantified by using ImageJ (http://rsb.info.nih.gov/ij/), for which stained gapdh, alpha-tubulin or ponceau S band strength was used as standard. The result was presented as mean value±standard deviation after being converted as relative percentage. The value of the protein showing the highest strength was considered as 100%. Comparison of statistics between two groups was performed by using Student's t-test. When P<0.05, it was judged as statistically significant. Analysis of results and statistics were performed under the same conditions.

Ninjurin1 and propidium iodide were double stained in the cross-section oculus extracted from mice at 1 day (P1), at 5 days (P5) and at 14 days (P14). Ninjurin1 and VE-cadherin in the oculus of the mouse at 5 days (P5) were double immunostained, followed by observation under fluorescent microscope.

Figure 2:
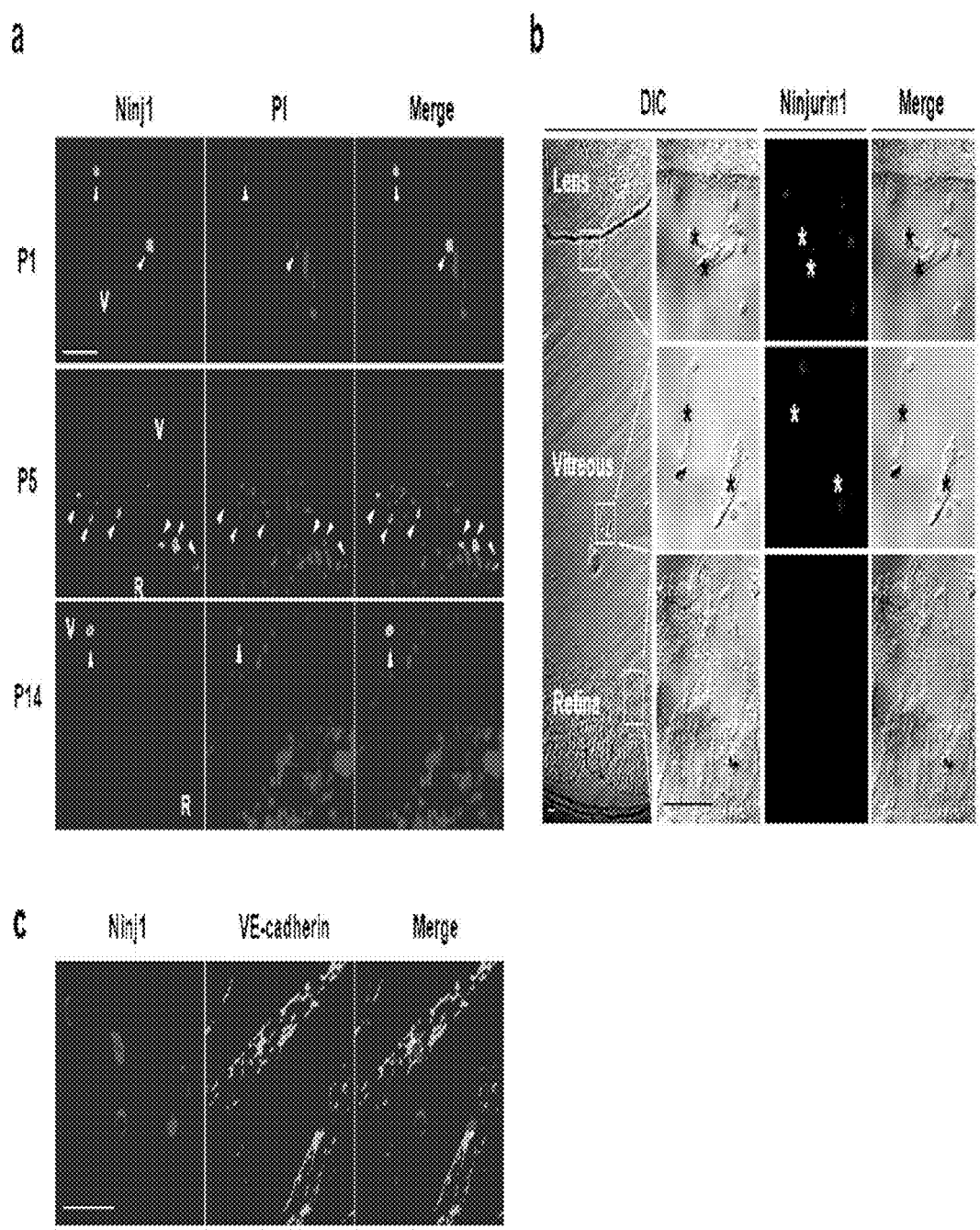
FIG. 2 is a set of diagrams illustrating the Ninjurin1 expression and location in the mouse oculus: (a) diagram showing cellular location where Ninjurin1 expression is observed in cross-sections of oculus of mice at 1 day (P1), at 5 days (P5) and at 14 days (P14) from birth. At this time, Ninjurin1 was stained green and nucleus was stained with propidium iodide (PI) (red); V: vitreous, R: retina, white arrow: cells expressing Ninjurin1. (b) diagram illustrating the DIC microscope imaging of the oculus, in which Ninjurin1 was stained red; (c) diagram illustrating Ninjurin1 (red) and VE-cadherin (green) in the oculus extracted from the mouse at 5 days (P5), observed by double immunostaining

As a result, as shown in FIG. 1 and FIG. 2, as ocular development progressed, density of blood vessel was reduced. Ninjurin1 protein expression was gradually increased up to 5 days from birth and the highest Ninjurin1 expression was observed in mice at 3 days and at 5 days, but thereafter the expression was gradually decreased (FIG. 1 and FIG. 2). The above results indicate that Ninjurin1 protein is most expressed in the early stage of ocular development.

Experimental Example 2

Ninjurin1 Expression Specific in Macrophages Around Blood Vessels

The present inventors performed double immunostaining of GS-lectin and Ninjurin1, Ninjurin1 and ConA, Ninjurin1 and F4/80, Ninjurin1 and Iba-I, and Ninjurin1 and NG2 in the cross-section oculus of the mouse at 5 days (P5). Then, expressions of those proteins were observed under fluorescent microscope.

Hyaloid vessels and structures were eliminated from the oculus using 5% gelatin and then GS-lectin and Ninjurin1 in the whole mount oculus were immuno-stained, followed by observation under fluorescent microscope.

As a result, as shown in FIG. 3 and FIG. 4, Ninjurin1 was expressed in macrophages around blood vessels but not in parenchymal microglia (FIG. 3 and FIG. 4). Therefore, Ninjurin1 protein was confirmed to be expressed specifically in macrophages around blood vessels.

Experimental Example 3

Effect of Ninjurin1 on Apoptosis of Vascular Endothelial Cells

GS-lectin and Ninjurin1 in vitreous of the mouse at 8 days (P8) were stained, followed by observation under fluorescent microscope.

Vitreous bodies of mice at 6 days (P6) and at 11 days (pll) were observed as the controls and oculus of mice at 6 days (p6) and at 11 days (pll) neutralized with a Ninjurin1 antibody were observed as the experimental group under immunofluorescent microscope.

Particularly, to block Ninjurin1 by using an antibody, 1 mg/kg of Ninjurin1 (BD) mouse neutralizing antibody or 1 mg/kg of mouse isotype control antibody (Santa Cruz) were intraperitoneally injected into mice at day 1 (P1). The mice were sacrificed at day 6 (P6) and at day 11 (P11). Blood vessels and macrophages in oculus were stained by using GS-lectin.

Figure 6:
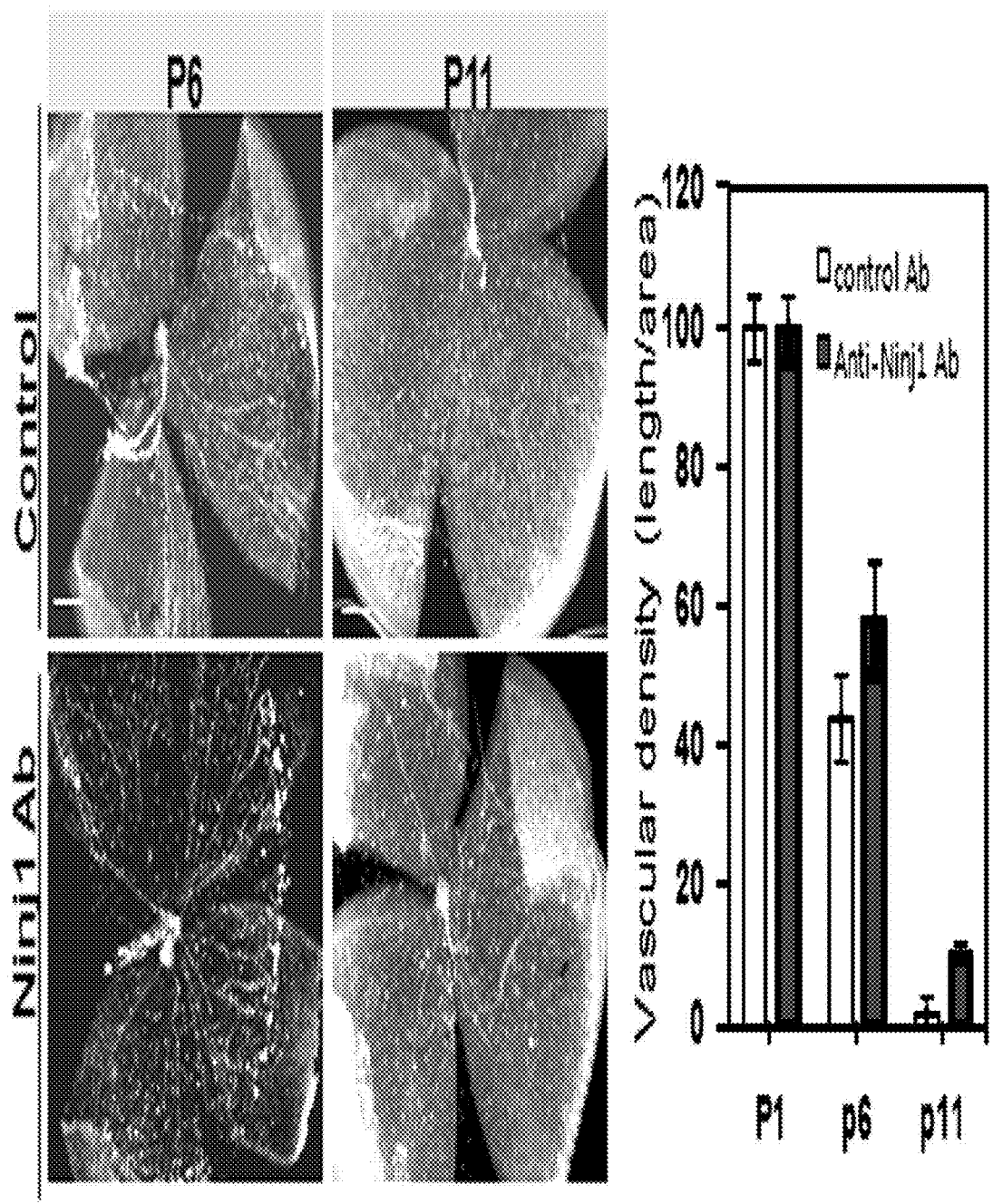
FIG. 6 is a diagram illustrating the changes of blood vessel density over Ninjurin1 expression, in which oculus of a mouse at 6 days (P6) belonging to the control and oculus of a mouse at 6 days (P6) neutralized with a Ninjurin1 antibody were stained with GS-lectin (green), followed by observation under fluorescent microscope.

As a result, as shown in FIG. 5 and FIG. 6, macrophages expressing Ninjurin1 were adhered on TUNEL positive vascular endothelial cells (proceeded to apoptosis) and the number of vascular endothelial cells was higher in the mouse group neutralized with a Ninjurin1 antibody than in the control group (FIG. 5 and FIG. 6). From the above results, it was confirmed that Ninjurin1 affected apoptosis of vitreous vascular endothelial cells and in the meantime Ninjurin1 neutralization by a Ninjurin1 antibody resulted in the decrease of vitreous vascular endothelial cells.

Experimental Example 4

Effect of Ninjurin1 on Cell-Cell Adhesion and Cell-Matrix Adhesion

The present inventors investigated cell adhesion by using BV2 cells transformed with pCS2+-Ninjurin1 or pCS2+-Mock.

Particularly, to investigate cell-cell adhesion, BV2 cells were stained with Hoechst (H33342) for 10 minutes, followed by washing with DMEM. The cells were detached by using trypsin/EDTA and those cells were distributed together with a neutralizing antibody in a 96-well plate (black bottom) on which a single layer of mouse brain microvascular endothelial cells was coated. The cells were lysed with 0.2% NP-40 and fluorescence of the lysate was measured at 340 nm by ELISA. To investigate cell-matrix adhesion, BV2 cells were loaded in a well plate coated with matrixes such as fibronectin (FN, Invitrogen), type I/IV collagen (col. I/col.IV, BD), gelatin (Sigma) and vitronectin (Vit, Invitrogen). After reaction for 15 minutes, the BV2 cells were washed with PBS twice. The adhered cells were stained with crystal violet, followed by washing twice again. The cells were lysed with 0.2% NP-40 and fluorescence of the lysate was measured at 590 nm by ELISA. At last, the cells transformed with Ninjurin1 and the cells not-transformed were mixed, followed by investigation of aggregate formation therein according to the conventional method (Araki T, et al., Neuron. 1996 August; 17(2): 353-61).

Figure 7:
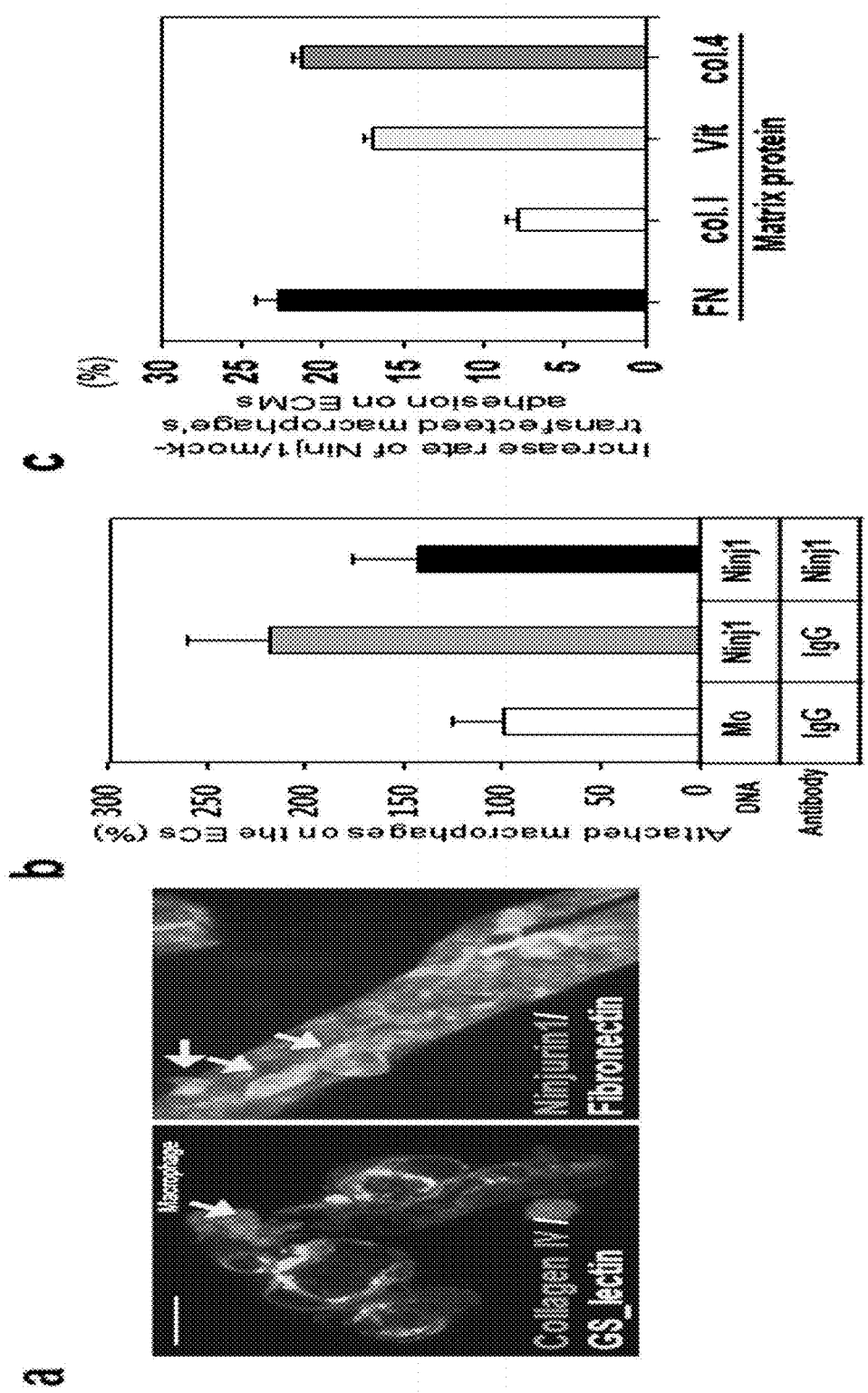
FIG. 7 is a set of diagrams illustrating the cell-matrix adhesion over Ninjurin1 expression: (a) diagram illustrating Type IV collage (red) and GS-lectin (green), and Ninjurin1 (red) and fibronectin (green) in the vitreous, observed under fluorescent microscope after double immunostaining; (b) graph illustrating the cell-matrix adhesion in BV2 cells transformed with pCS2+-Ninjurin1 and in BV2 cells transformed with pCS2+-Mock which were both neutralized by a Ninjurin1 antibody and control IgG respectively; and (c) graph illustrating the result of investigation of adhesion of BV2 cells transformed with pCS2+-Ninjurin1 and BV2 cells transformed with pCS2+-Mock to different matrixes (FN: fibronectin; Col. I: type I collagen; Vit: vitronectin; Col. IV: type IV collagen).
Figure 8:
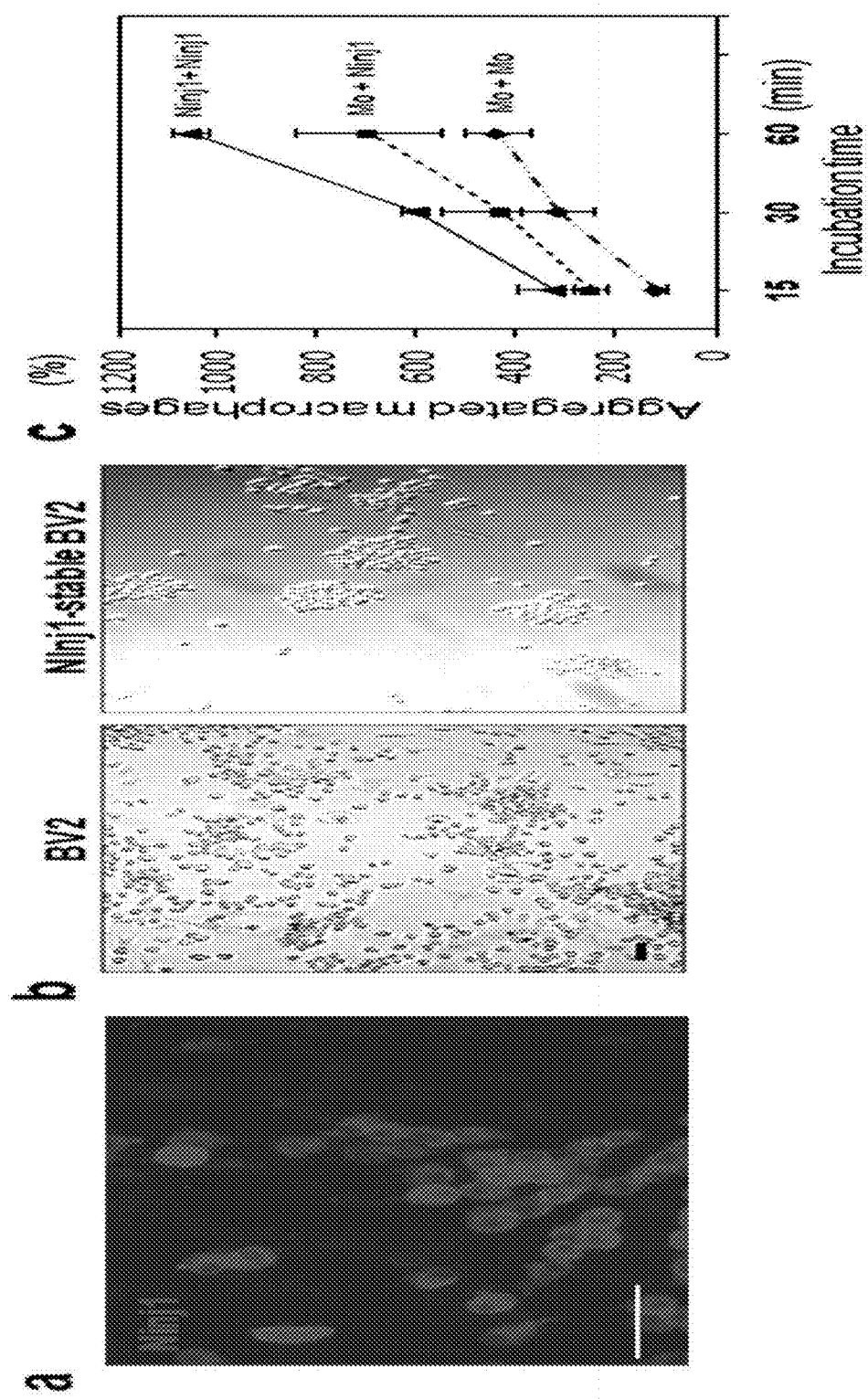
FIG. 8 is a set of diagrams illustrating the cell-cell adhesion over Ninjurin1 expression; (a) diagram illustrating that Ninjurin1 (red) in the vitreous of the mouse at 3 days (P3) was stained, followed by observation under fluorescent microscope; (b) diagram illustrating the coagulation of wild type BV2 cells and BV2 cells (Ninj1-stable BV2) expressing Ninjurin1 constantly, observed after 2 day culture; and (c) graph illustrating the coagulation of cultured Mock-Ninjurin1 expressing cell mixture.

As a result, as shown in FIG. 7, Ninjurin1 expression increased macrophage-vascular endothelial cell adhesion. And, cell-matrix adhesion in BV2 cells expressing Ninjurin1 was greater than in BV2 cells expressing mock. When BV2 cells were neutralized with a Ninjurin1 antibody, cell-matrix adhesion capacity of the cells was reduced (FIG. 7). As shown in FIG. 8, BV2 cells expressing Ninjurin1 formed an aggregate around vascular cells, that is the cells were growing with forming an aggregate (FIG. 8).

Therefore, it was confirmed that Ninjurin1 induced cell-cell aggregation and accelerated cell-matrix adhesion.

Experimental Example 5

Effect of Ninjurin1 on Wnt-Ang Signal Transduction System

The present inventors performed RT-PCR and real-time PCR to investigate Wnt7b expression in BV2 cells transformed with Myc-mock or Myc-Ninjurin1 labeled DNA and Wnt7b expression in cells in which Ninjurin1 expression was inhibited by using siRNA.

Particularly, RT-PCR and real time PCR were performed as follows: Transformed BV2 cells were cultured in DMEM supplemented with 1% serum for 2 days, and then RNA was extracted by using Trizol reagent (Invitrogen). Following primers were used for RT-PCR: Gapdh: forward primer 5'-ACCACAGTCCATGCCATCAC-3' (SEQ. ID. NO: 4), reverse primer 5'-TCCACCACCCTGTTGCTGTA-3' (SEQ. ID. NO: 5); Ninjurin1: forward primer 5'-GAGTCGGGCACTGAGGA-3' (SEQ. ID. NO: 6), reverse primer: 5'-GTTGCAGGGGTCTGGTCA-3' (SEQ. ID. NO: 7); Ang1: forward primer 5'-AGGCTTGGTTTCTCGT-CAGA-3' (SEQ. ID. NO: 8), reverse primer: 5'-TCTGCA-CAGTCTCGAAATGG-3' (SEQ. ID. NO: 9); Ang2: forward primer 5'-GCTGCTGGTTTATTACTGAAGAA-3' (SEQ. ID. NO: 10), reverse primer: 5'-TCAGGTGGACTGGGAT-GTTTAG-3' (SEQ. ID. NO: 11); Wnt7b: forward primer 5'-AAGAACTCCGAGTAGGGAGTCG-3' (SEQ. ID. NO: 12), reverse primer: 5'-TGCGTTGTACTTCTCCTTGAGC-3' (SEQ. ID. NO: 13); Wnt7b: $2^{nd}$ round forward primer 5'-CCGAGTAGGGAGTCGAGAGG-3' (SEQ. ID. NO: 14), reverse primer: 5'-CACACCGTGACACTTACATTCC-3' (SEQ. ID. NO: 15). The PCR products were separated on 1.2% agarose gel containing EtBr (ethidium bromide), followed by analysis by digital imaging. Primers used for real-time PCR were as follows: Ang2: forward primer 5'-TGT-GATCTTGTCTTGGCCGC-3' (SEQ. ID. NO: 16), reverse primer: 5'-AGAGGGAGTGTTCCAAGAAGC-3' (SEQ. ID.

NO: 17); Gapdh, Ang1 and Wnt7: same primers as used for RT-PCR were used. Conditions for RT-PCR and real-time PCR were the same.

Wnt7b expression in BV2 cells transformed with Myc-mock or Myc-Ninjurin1 labeled DNA was observed under immunofluorescent microscope.

Figure 9:
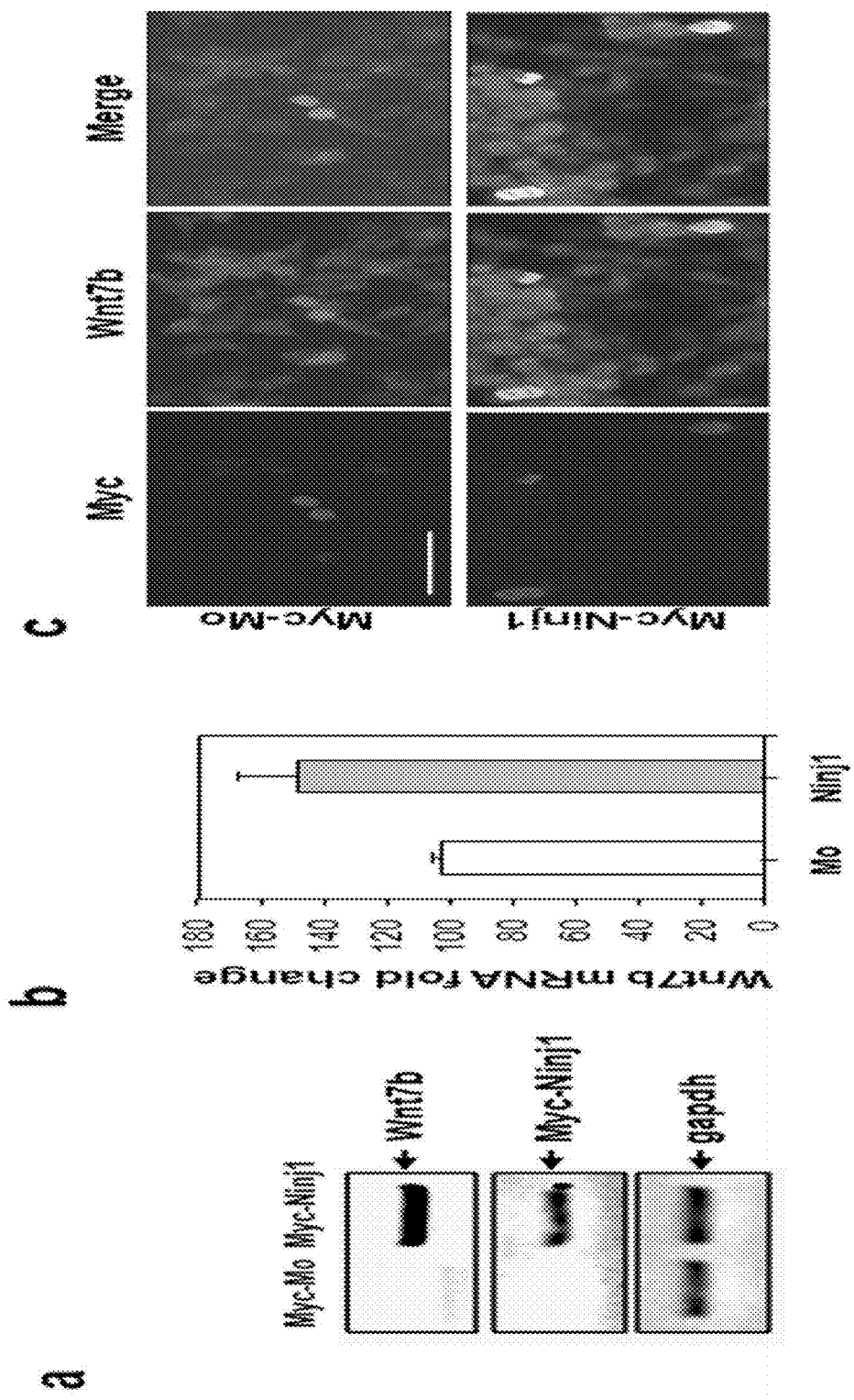
FIG. 9 is a set of diagrams illustrating the Wnt7b expression over Ninjurin1 expression: (a) diagram illustrating the result of RT-PCR, in which Wnt7b expressions in BV2 cells expressing Myc-mock and BV2 cells expressing Myc-Ninjurin1 were shown; (b) diagram illustrating the result of real-time PCR; and (c) diagram illustrating the result of immunostaining examining the expressions of Wnt7b (green) and c-Myc (red).
Figure 10:
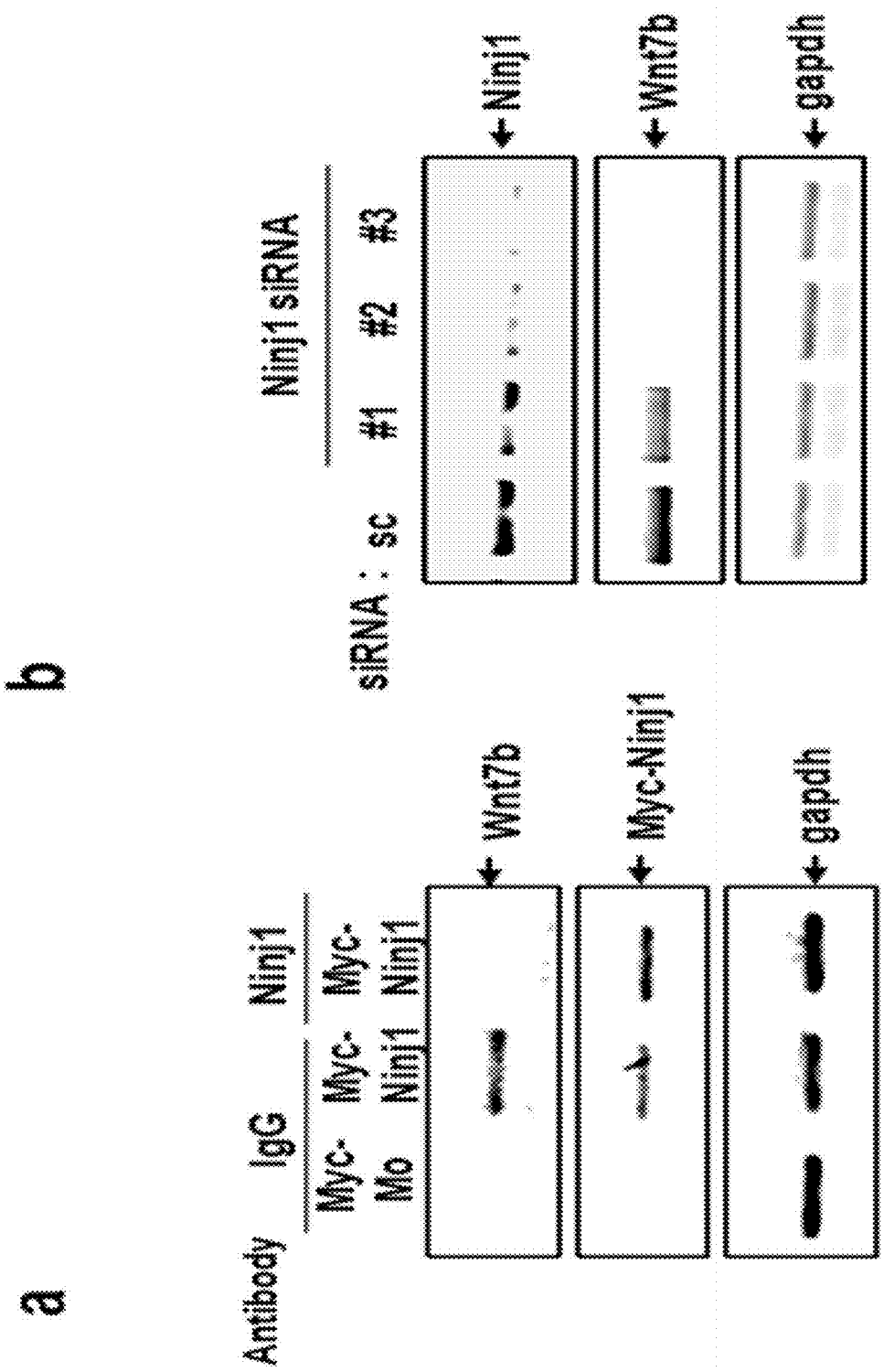
FIG. 10 is a set of diagrams illustrating the Wnt7b expression over Ninjurin1 expression: (a) diagram illustrating the result of RT-PCR investigating Wnt7b expression in BV2 cells expressing Myc-Ninjurin1 neutralized with Ninjurin1 antibody; and (b) diagram illustrating the result of RT-PCR examining Wnt7b expression in BV2 cells in which Ninjurin1 was suppressed by siRNA.

As a result, as shown in FIG. 9 and FIG. 10, Wnt7b expression was increased in BV2 cells expressing Ninjurin1, compared with in BV2 cells expressing mock. In the meantime, when Ninjurin1 expression was inhibited, Wnt7b expression was reduced (FIG. 9 and FIG. 10).

To investigate the effect of Ninjurin1 on the expressions of p38, MAPK (p44/p42) and JNK (p54/46), Western blotting was performed with the lysate of BV2 cells transformed with Myc-mock or Myc-Ninjurin1 labeled DNA. The BV2 cells transformed with Myc-mock or Myc-Ninjurin1 labeled DNA were treated with SB203580, the p38 inhibitor, at different concentrations (0, 10, and 30 uM), followed by investigation of Wnt7b expression.

Figure 11:
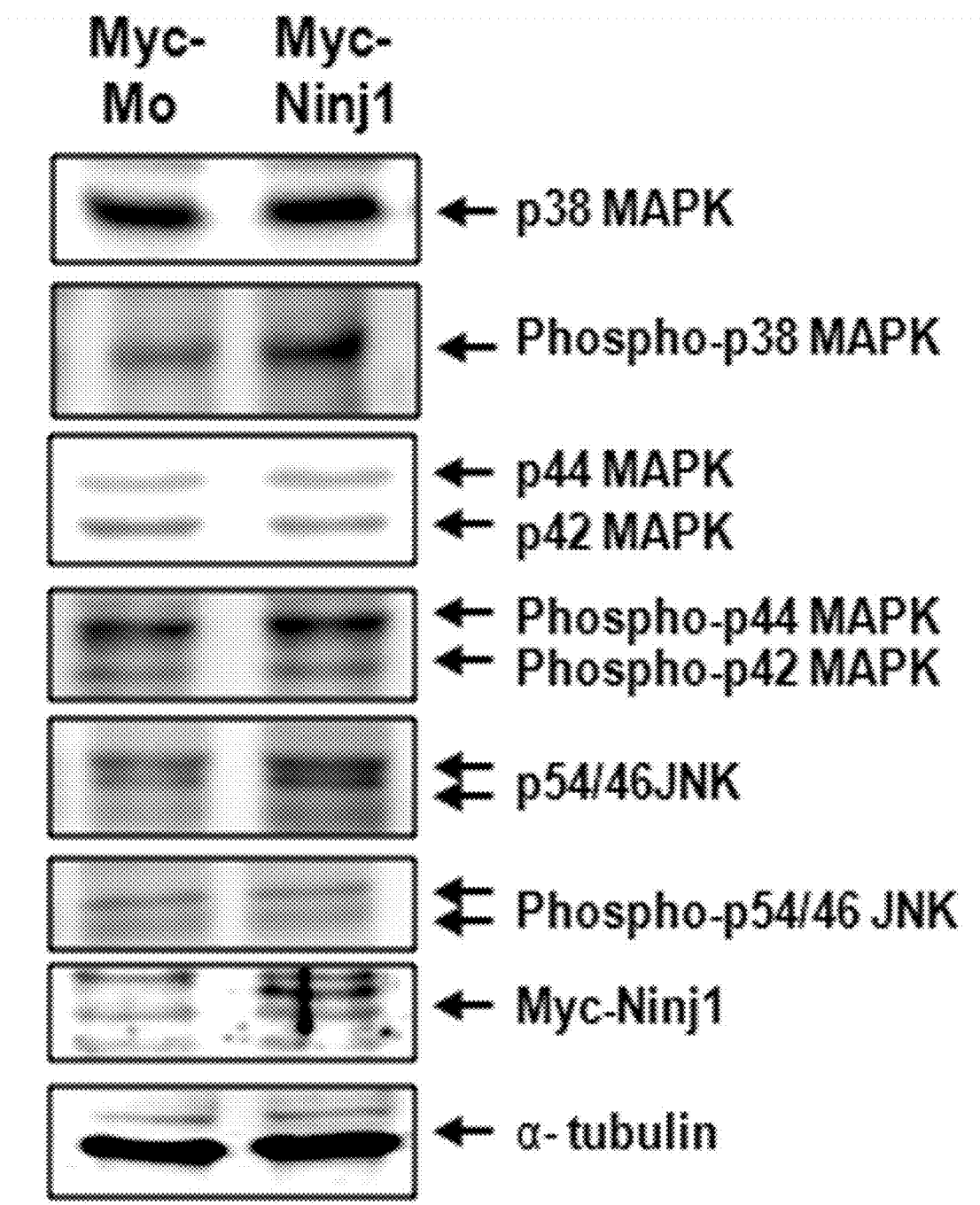
FIG. 11 is a diagram illustrating the expressions of p38, MAPK (p44/p42) and JNK (p54/46) over Ninjurin1 expression. This picture shows the result of Western blotting with cell lysate of BV2 cells expressing Myc-mock and BV2 cells expressing Myc-Ninjurin1.
Figure 12:
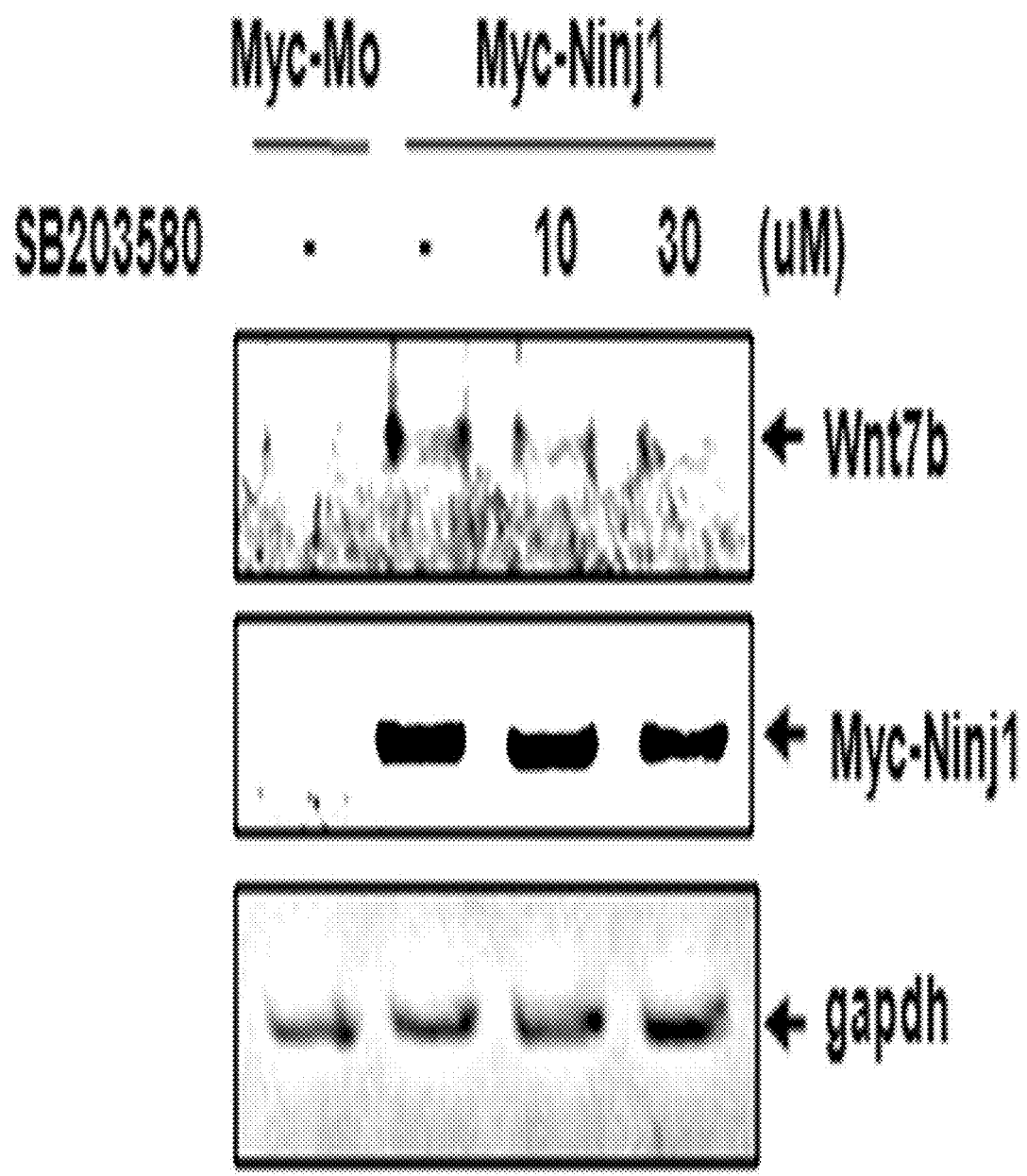
FIG. 12 is a diagram illustrating the Wnt7b expression according to the inhibition of p38 expression. BV2 cells expressing Myc-mock and BV2 cells expressing Myc-Ninjurin1 were treated with SB203580, the p38 inhibitor, at different concentrations, followed by RT-PCR examining the expression of Wnt7b.

As a result, as shown in FIG. 11, expressions of phosphorylated p38, MAPK (p44/p42) and JNK (p54/46) were increased in BV2 cells expressing Ninjurin1, compared with in BV2 cells expressing mock (FIG. 11). As shown in FIG. 12, Wnt7b expression stimulated by Ninjurin1 was reduced by the p38 inhibitor dose-dependently (FIG. 12).

To investigate the effect of Ninjurin1 on the expressions of Ang1 and Ang2, the culture solution of BV2 cells transformed with Myc-mock or Myc-Ninjurin1 labeled DNA were treated to human pericytes, followed by RT-PCR and real-time PCR to examine the expressions of angiopoietin-1 (Ang1) and angiopoietin-2 (Ang2).

Figure 13:
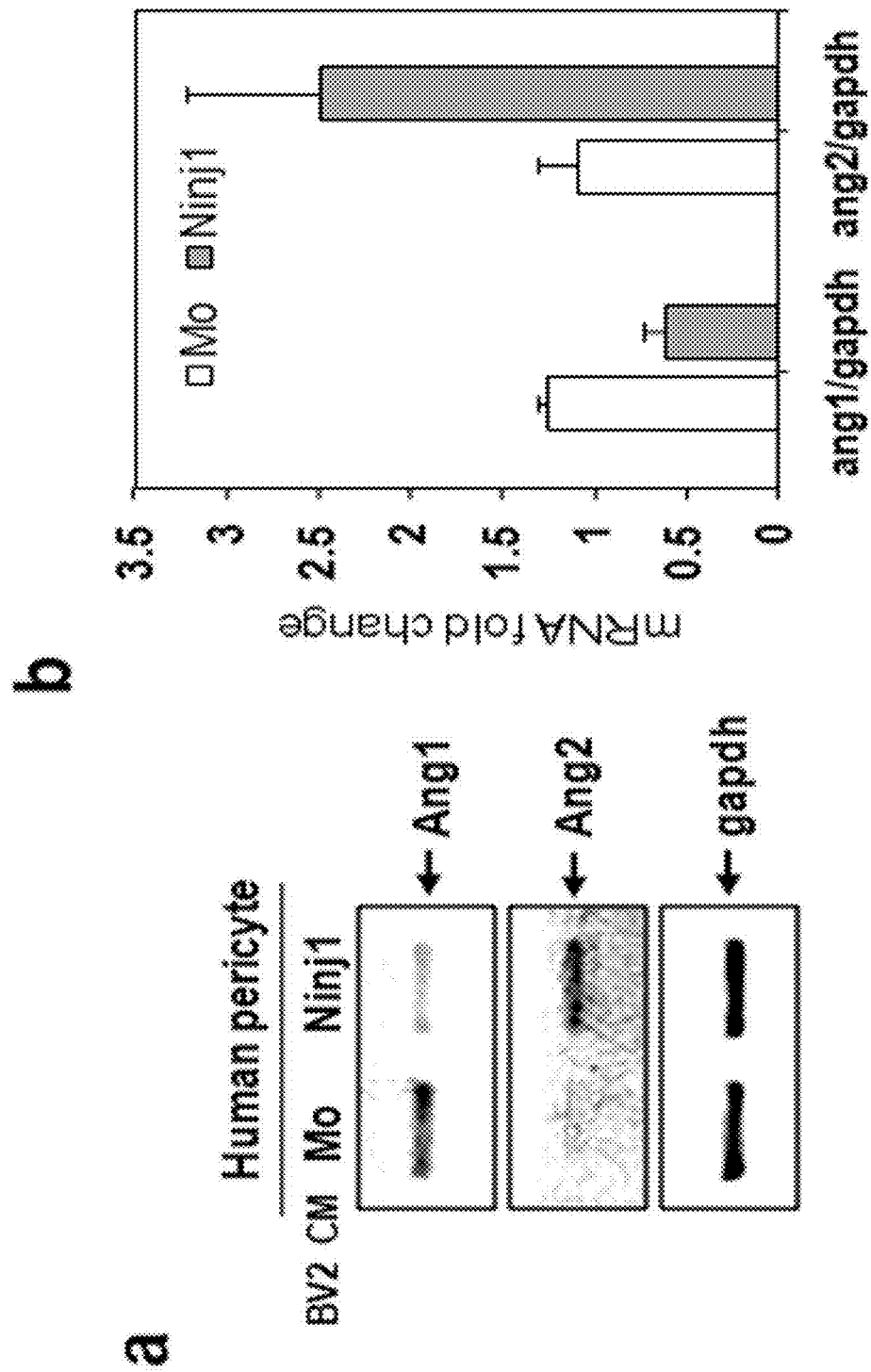
FIG. 13 is a diagram illustrating the expressions of Ang1 and Ang2 over Ninjurin1 expression. Pericytes were treated with culture solutions of BV2 cells expressing Myc-mock and BV2 cells expressing Myc-Ninjurin1, followed by RT-PCR (left) and real-time PCR (right) to investigate Ang1 and Ang2 expressions.

As shown in FIG. 13, Ang1 expression was reduced in pericytes treated with culture solution of BV2 cells expressing Ninjurin1, compared with in pericytes treated with culture solution of BV2 cells expressing mock, but Ang2 expression was increased in pericytes treated with culture solution of BV2 cells expressing Ninjurin1, compared with in pericytes treated with culture solution of BV2 cells expressing mock (FIG. 13).

To investigate interaction among Wnt7b, Ninjurin1, Ang1 and Ang2, Wnt7b and Ninjurin1 were quantified by RT-PCR in the presence of recombinant human Ang1 (rh-Ang1) and rh-Ang2 at different concentrations (0, 1 and 2.5 ug/ml) in rodent originated macrophages (Raw264.7, BV2).

Figure 14:
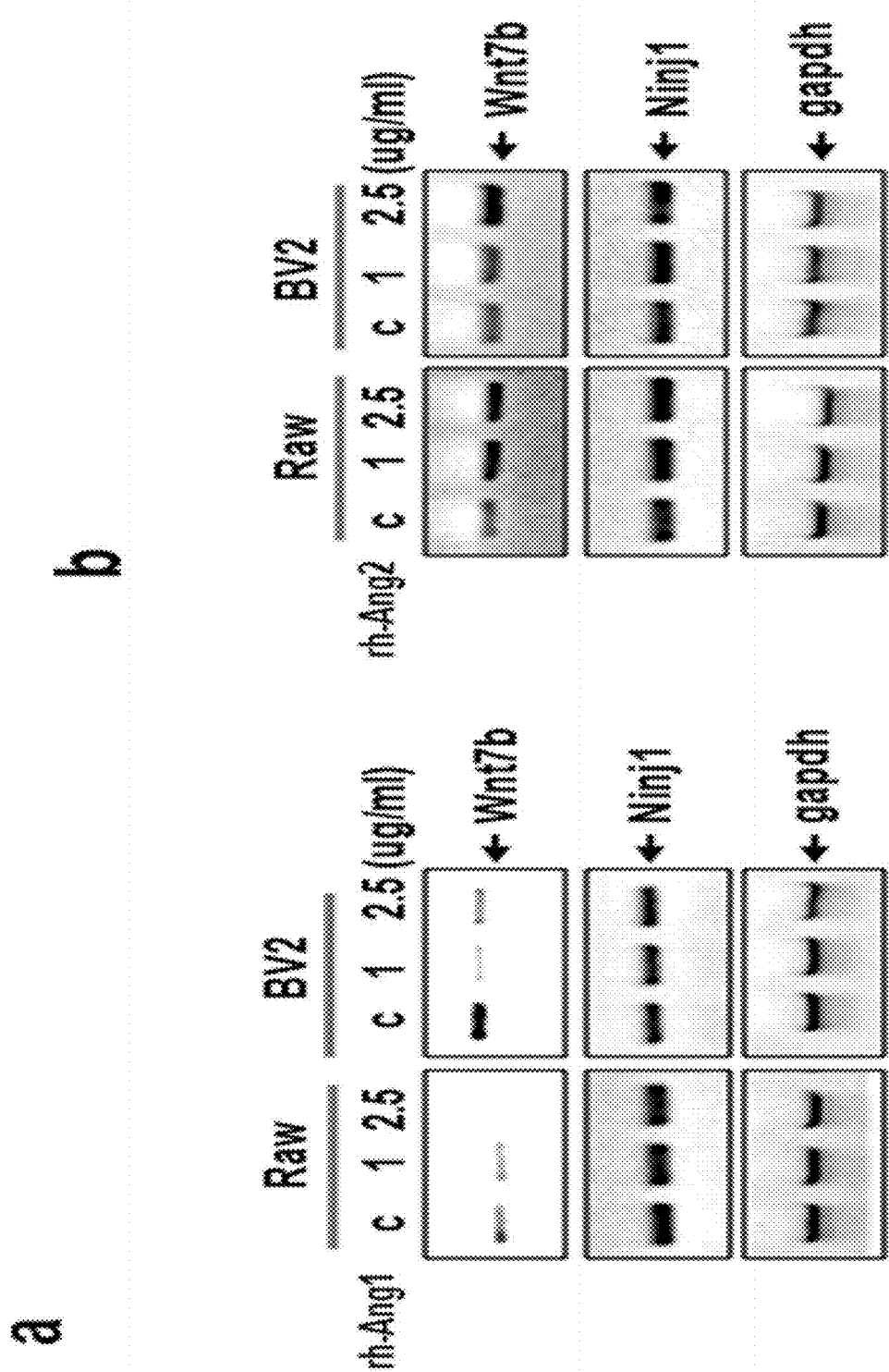
FIG. 14 is a diagram illustrating the levels of Wnt7b and Ninjurin1 according to the concentrations of Ang1 and Ang2 in rodent originated macrophages (Raw264.7, BV2) and BV2 cells. RT-PCR was performed to quantify Wnt7b and Ninjurin1 affected by different concentrations of recombinant human Ang1 (rh-Ang1) (left) and by different concentrations of recombinant human Ang2 (rh-Ang2) (right).

As shown in FIG. 14, Wnt7b and Ninjurin1 expressions were reduced by rh-Ang1 dose-dependently, but increased by rh-Ang2 dose-dependently (FIG. 14).

Figure 15:
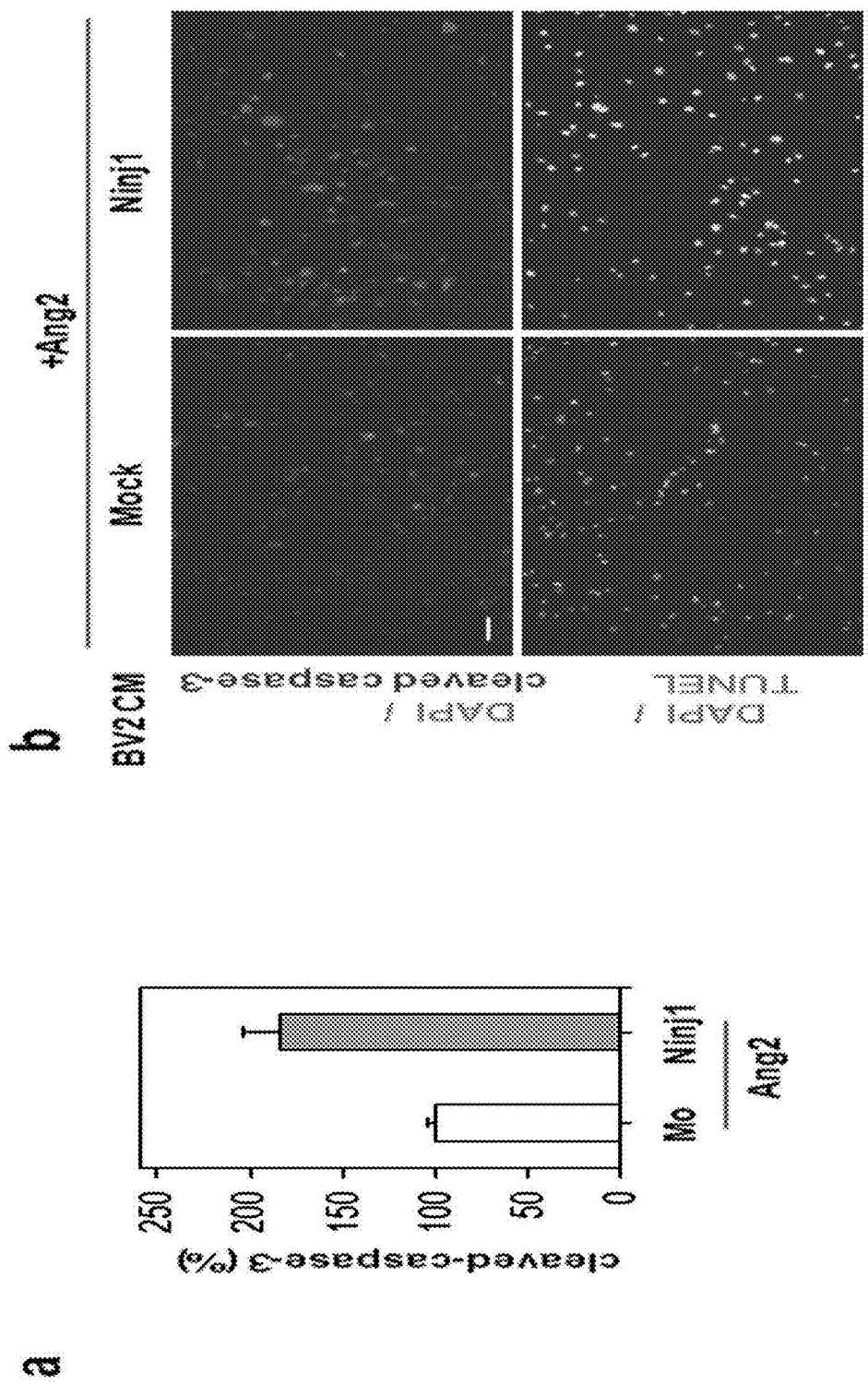
FIG. 15 is a set of diagrams illustrating the caspase 3 digestion and apoptosis by Ninjurin1 in HUVEC cells in the presence of rh-Ang2: (a) diagram illustrating the result of Western blotting examining caspase 3 digestion in HUVEC cells treated with culture solutions of BV2 cells expressing Myc-mock and BV2 cells expressing Myc-Ninjurin1; and (b) diagram illustrating the result of immunostaining showing caspase 3 (red), TUNEL (green) and nucleus (blue) in HUVEC cells treated with culture solutions of BV2 cells expressing Myc-mock and BV2 cells expressing Myc-Ninjurin1.

HUVEC cells were treated with culture solution of BV2 cells transformed with Myc-mock or Myc-Ninjurin1 labeled DNA in the presence of rh-Ang2 for 24 hours. Then, caspase 3 digestion in HUVEC cells was confirmed by Western blotting. And the caspase 3 digestion and TUNEL were confirmed by immunofluorescence staining As shown in FIG. 15, caspase 3 digestion and apoptosis were increased in HUVEC cells treated with culture solution of BV2 cells expressing Ninjurin1, compared with in HUVEC cells treated with culture solution of BV2 cells expressing mock in the presence of rh-Ang2 (FIG. 15).

Therefore, it was confirmed that Ninjurin1 expression increases Wnt7b expression, reduces Ang1 expression but increases Ang2 expression, and activates p38, MAPK (p44/42) and JNK (p54/46). That is, Ninjurin1 regulates Wnt-Ang signal transduction system and causes apoptosis of vascular endothelial cells by Ang2.

Experimental Example 6

Ninjurin1 Expression Pattern Under Inflammatory Condition Induced by LPS

To induce inflammation in vivo, lipopolysaccharide (LPS) (lipopolysaccharides from *Escherichia coli* 0111:B4, Sigma) was intraperitoneally injected into Sprague-Dawley (SD) line SPF rat. Oculus was extracted from the rat, followed by immunofluorescence staining (Ninjurin1 and Iba-1 were stained) to investigate Ninjurin1 expression (Ninjurin1 stained), and inflow and activation of macrophages and microglias (Iba-I stained).

Figure 16:
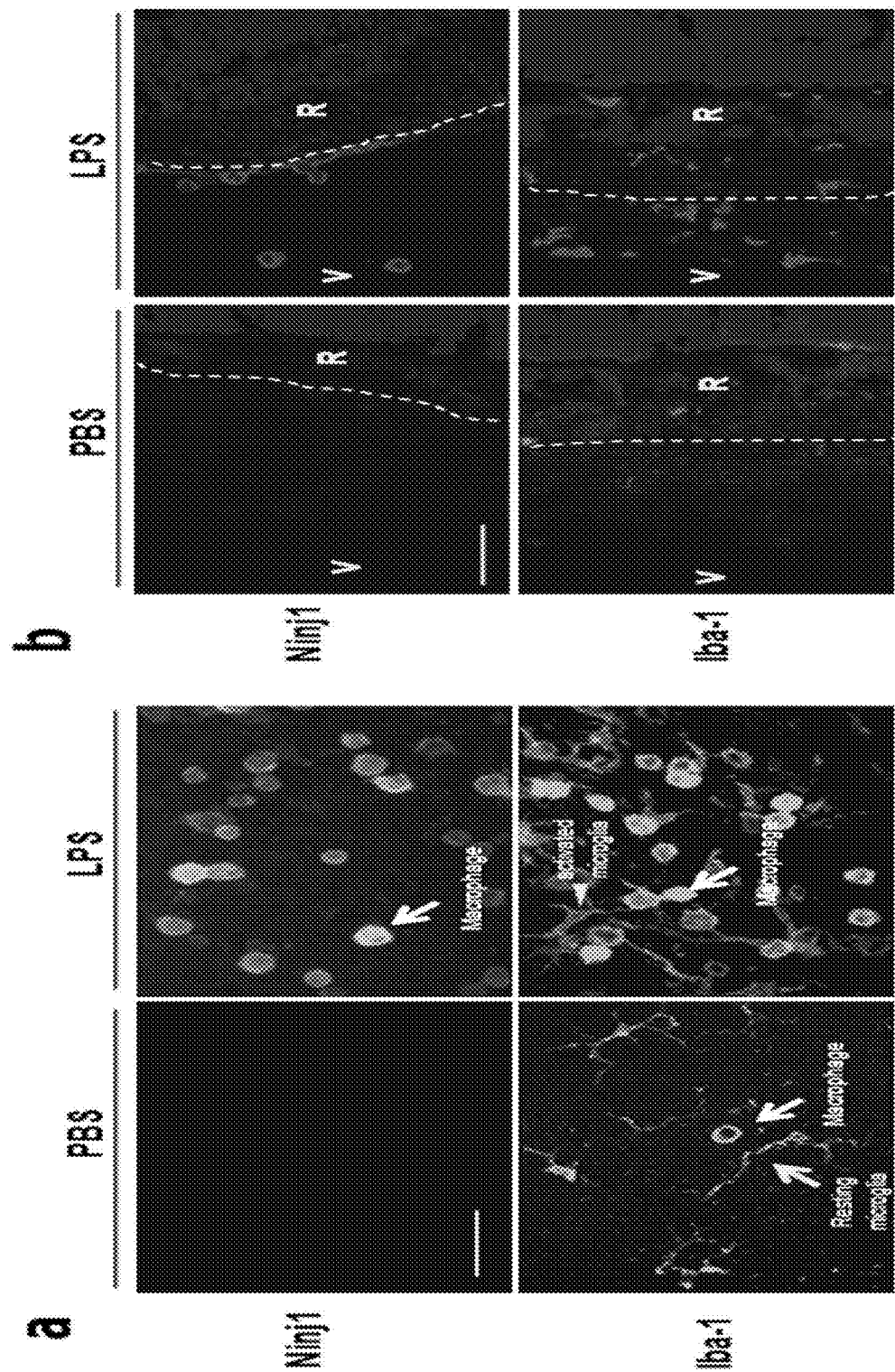
FIG. 16 is a set of diagrams illustrating the Ninjurin1 expression under the inflammation condition induced by intraperitoneal injection of LPS into Sprague-Dawley (SD) line SPF rat: (a) diagram illustrating the result of immunostaining of the rat oculus with Iba-1 (green). The rat was administered with LPS to induce systemic inflammation; and (b) diagram illustrating the result of immunostaining of vitreous of the oculus with Iba-1, in which Ninjurin1 was stained red.

As a result, as shown in FIG. 16, the cells expressing Ninjurin1 were observed in vitreous after LPS injection and inflow of ovoid macrophages was accelerated and at the same time microglias stretching their arms were changed into activated microglias. That is, LPS injection resulted in the increase of inflow and activation of macrophages and microglias and round shaped macrophages expressing Ninjurin1 were observed in retina (FIG. 16).

Therefore, it was confirmed that when inflammation was induced by LPS, the number of macrophages expressing Ninjurin1 were increased and Ninjurin1 expression was also increased.

Experimental Example 7

Inflammation Related Protein Expression Over Ninjurin1 Expression

To induce inflammation in vitro, BV2 cells were treated with LPS at different concentrations (0, 1, and 2.5 ug/ml), followed by Western blotting and RT-PCR to investigate iNOS expression, the index for inflammation, and Ninjurin1 expression.

As shown in FIG. 17, iNOS was up-regulated by LPS injection and Ninjurin1 expression was also increased by LPS dose-dependently (FIG. 17).

To investigate the effect of Ninjurin1 expression on iNOS expression, Western blotting and RT-PCR were performed to measure iNOS expression in BV2 cells transformed with Myc-mock or Myc-Ninjurin1 labeled DNA.

As shown in FIG. 18, iNOS expression was increased in BV2 cells over-expressing Ninjurin1, compared in BV2 cells expressing mock. iNOS expression was increased as Ninjurin1 expression was increased (FIG. 18).

To investigate the effect of Ninjurin1 expression on the generation of NO, the inflammatory mediator, NO generation was measured in BV2 cells transformed with Myc-mock or Myc-Ninjurin1 labeled DNA.

Particularly, NO generation was calculated by measuring nitrite, the stable reaction product of NO in the cell culture solution, by using Griess reagent. 100 μl of cell culture solution was mixed with 100 μl of Griess reagent [1% sulfanilamide dissolved in 30% acetate and 0.1% N-(1-naphthyl) ethylenediamine dissolved in 60% acetate, 1:1]. 10 minutes later, $OD_{570}$ was measured by ELISA (Ebert S, et al., *J. Neuroimmunol.* 2005 February; 159(1-2): 87-96). The acetate, sulfanilamide and N-(1-naphthyl)ethylenediamine were purchased from Sigma.

Figure 19:
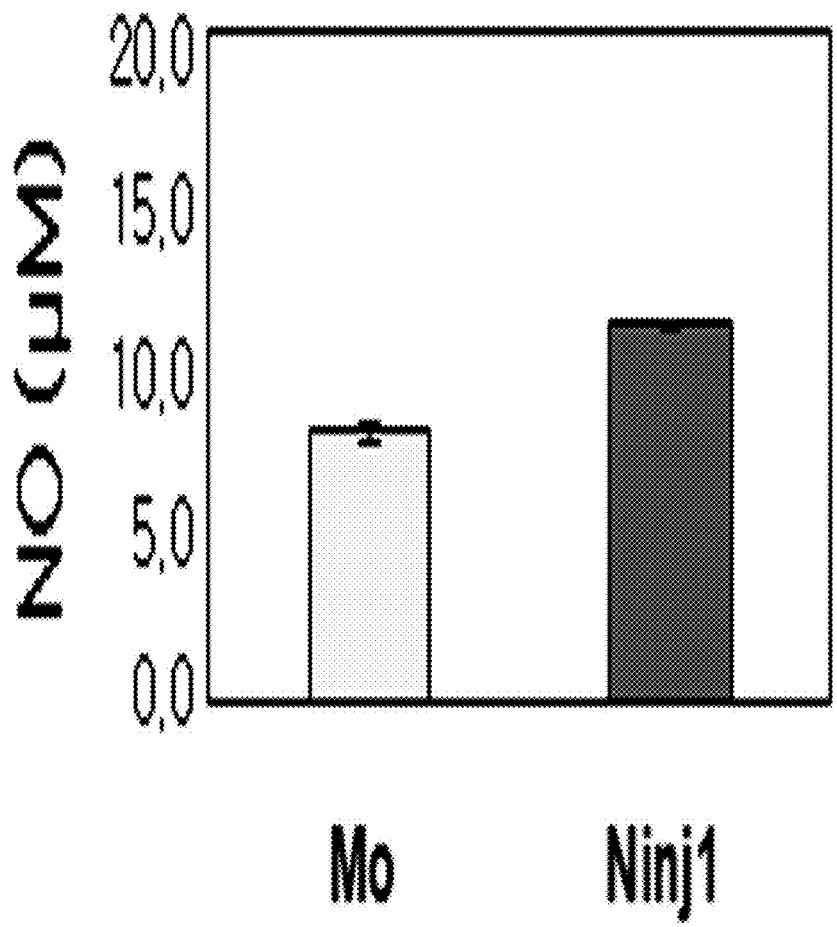
FIG. 19 is a diagram illustrating the generation of NO, the inflammatory mediator, over Ninjurin1 expression. NO levels in BV2 cells expressing Myc-mock and BV2 cells expressing Myc-Ninjurin1 were quantified by using Griess reagent.

As shown in FIG. 19, NO generation was increased in BV2 cells over-expressing Ninjurin1, compared in BV2 cells expressing mock (FIG. 19).

To investigate the effect of Ninjurin1 expression inhibition on iNOS expression, siRNA and shRNA were respectively inserted into a vector, which were inserted into BV2 cells.

Then, Ninjurin1 and iNOS expressions in the BV2 cells where Ninjurin1 expression was inhibited were quantified by Western blotting and RT-PCR.

Figure 20:
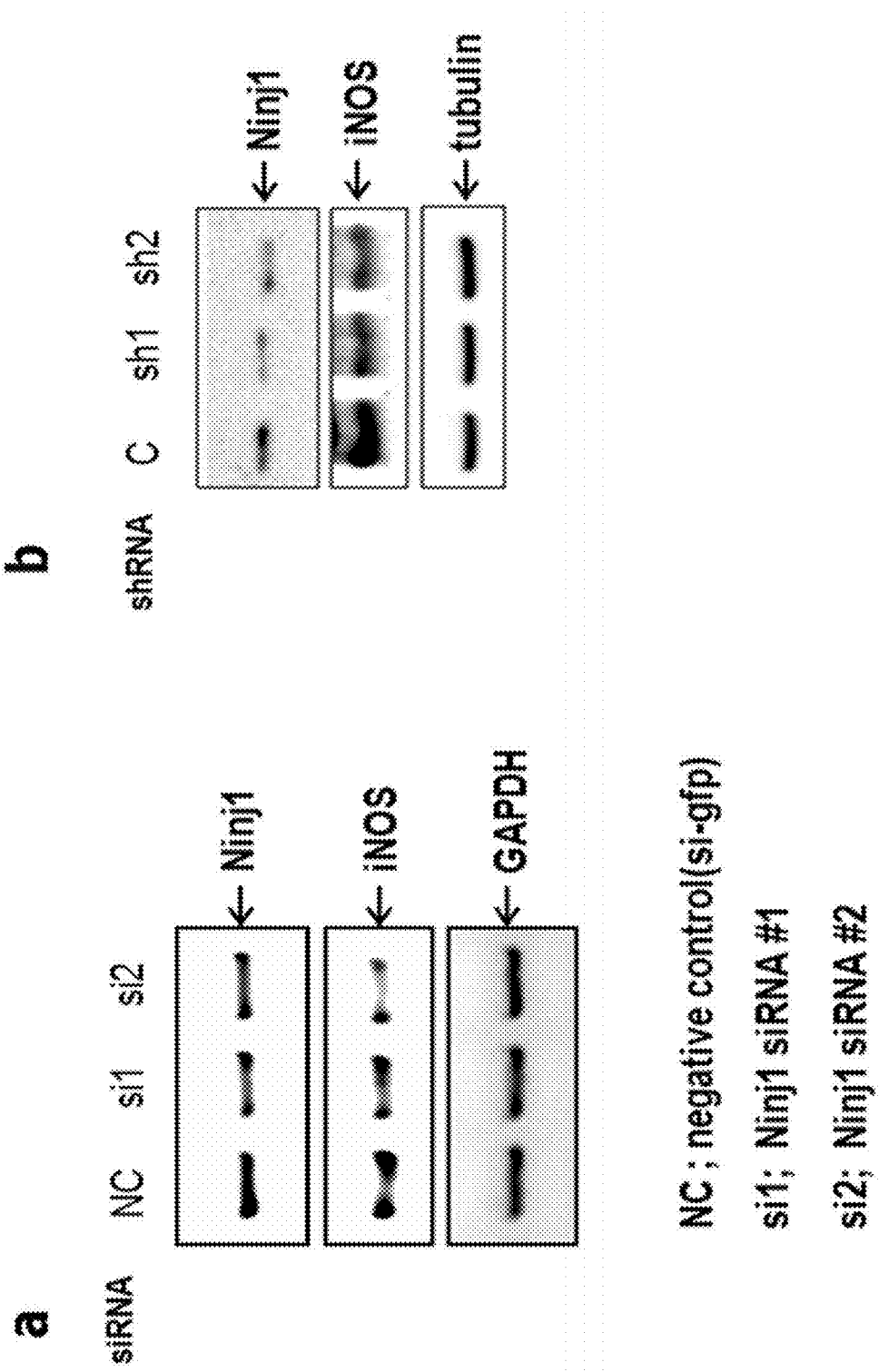
FIG. 20 is a set of diagrams illustrating the iNOS expression according to the decrease of Ninjurin1 expression: (a) diagram illustrating the result of RT-PCR examining iNOS expression when Ninjurin1 expression was inhibited by siRNA in BV2 cells expressing Ninjurin1; and (b) diagram illustrating the result of RT-PCR examining iNOS expression when Ninjurin1 expression was inhibited by shRNA in BV2 cells expressing Ninjurin1.

As a result, as shown in FIG. 20, Ninjurin1 expression was significantly reduced by siRNA and shRNA and accordingly iNOS expression was reduced (FIG. 20).

Therefore, it was confirmed that Ninjurin1 over-expression increased expression of iNOS, the inflammation index and increased generation of NO, the inflammatory mediator. On the other hand, inhibition of Ninjurin1 expression resulted in the decrease of iNOS expression. The above results suggest that Ninjurin1 is deeply involved in inflammation reaction.

The Manufacturing Examples of the composition for the present invention are described hereinafter.

Experimental Example 8

Ninjurin1 Expression in Normal Rat Brain

The present inventor investigated Ninjurin1 expression in the normal Lewis rat brain through microscopy after immunohistochemical staining Lewis rats were purchased from Orient Bio., Inc., Korea and maintained under pathogen-free conditions in the animal housing facilities of the College of Pharmacy, Seoul National University for the period of the experiments by the Committee for Care and Use of Laboratory Animals at Seoul National University (SNU-090316-9).

Figure 21:
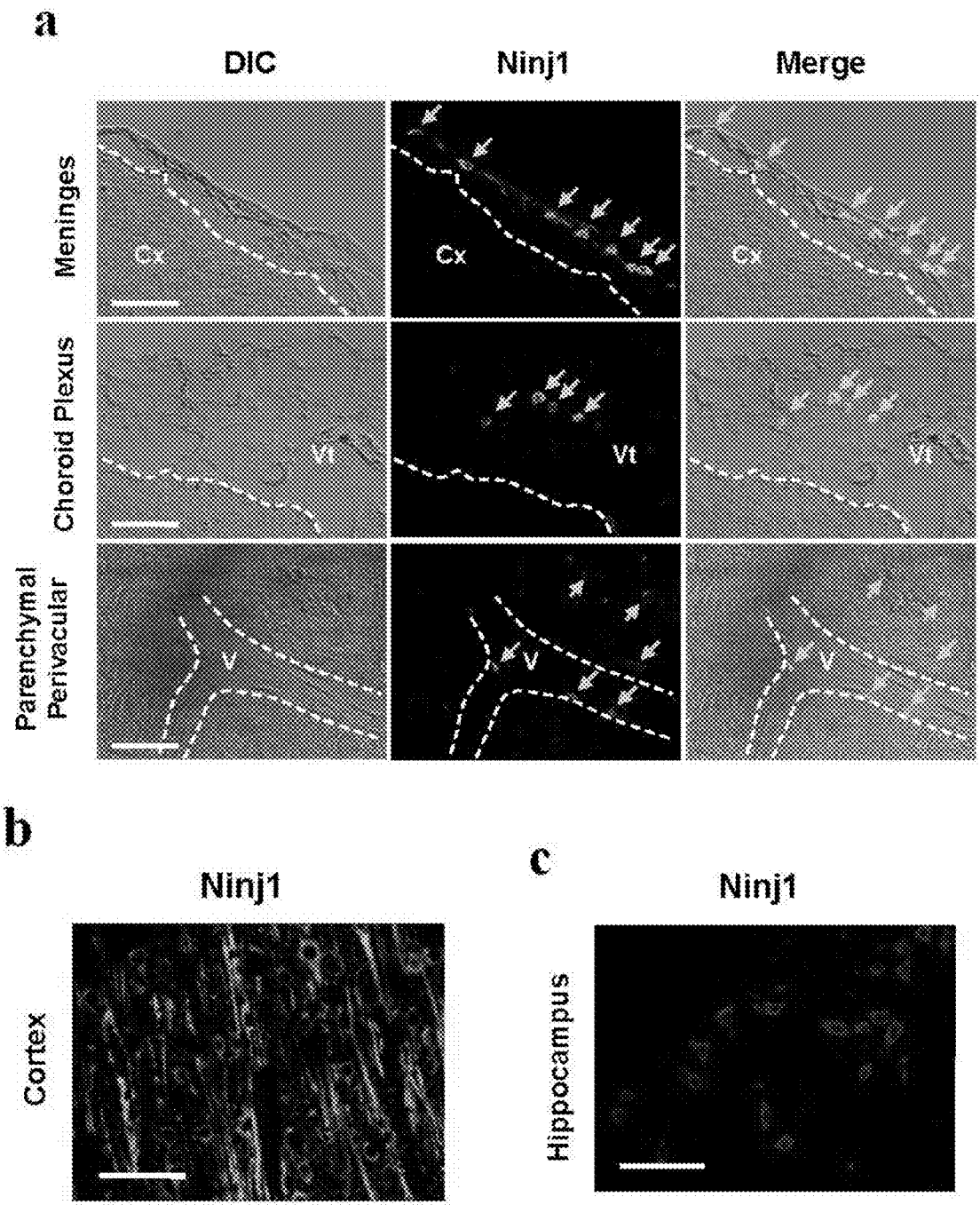
FIG. 21 shows the location of Ninjurin1 expressing cells (a), and the weak expression of Ninjurin1 in the cerebral cortex (b) and in hippocampal regions (c).

Particularly, 8 weeks female rat was sacrificed and extracted its brain. The brain fixed in 4% PFA was sliced as 30 um thick and stored in 4° C. Storing buffer. Rabbit anti-rat Ninjurin1 (gift from Dr. J. Milbrant) was incubated for overnight in 4° C. as primary antibody and Alexa 488-conjugated IgG and Alexa 546-conjugated IgG were incubated for 1 h in room temperature as secondary antibody. Inventor visualized Ninjurin1 expression in normal rat brain using Axiovert M200 microscopy after immunostaining Ninjurin1 expressing cells were located in three distinct regions of brain, including meninges, the choroid plexus, and the parenchymal perivascular region (FIG. 21A, green, yellow allow). Also inventor absorbed that Ninjurin1 was weakly expressed in the cerebral cortex (FIG. 21B) and in hippocampal regions (FIG. 21C).

Experimental Example 9

Ninjurin1 Expression in EAE Rat Brain and Blood

The present inventor thought that Ninjurin1 might be expressed in immune cell within blood. So they compared Ninjurin1 expression in rat brain of EAE (experimental autoimmune encephalomyelitis), that is mainly caused by immune cell infiltration from blood. To construct EAE rat animal model, female Lewis rats weighing 160-200 g and aged 6-10 weeks were immunized subcutaneously with an emulsion containing 25 μg of guinea pig myelin basic protein (MBP)68-86 in complete Freund's adjuvant (CFA; *Mycobacterium tuberculosis* H37Ra, 4 mg/mL). Each animal was injected with 2 μg of Pertussis Toxin intraperitoneally at the time of immunization. Rats were weighed and observed daily for clinical signs of EAE. The progression of EAE was graded according to the following scale: 0, no symptoms; 1, floppy tail; 2, mild paralysis of hind limbs; 3, complete paralysis of hind limbs; 4, complete paralysis of hind limbs with forelimb involvement; 5, moribund state or death. Rats reaching a score of 3 with complete paralysis of hind limbs were killed under ether anesthesia and sliced through the procedures of experimental example 1 (FIG. 22A).

Furthermore, total RNA from the blood of normal and EAE rats was purified using Trizol (Invitrogen) and performed RT-PCR analysis as following primer.

```
Gapdh (loading control):
                                 (SEQ. ID. NO.: 4)
    sense         5'-ACCACAGTCCATGCCATCAC-3', (SEQ. ID. NO.: 5)
    antisense     5'-TCCACCACCCTGTTGCTGTA-3'.

Ninjurin1:
                                 (SEQ. ID. NO.: 18)
    sense         5'-CATCTCTCTCGTGCTGCA-3', (SEQ. ID. NO.: 19)
    antisense     5'-GCCAAGAGACACTGCCAA-3'.
```

Figure 22:
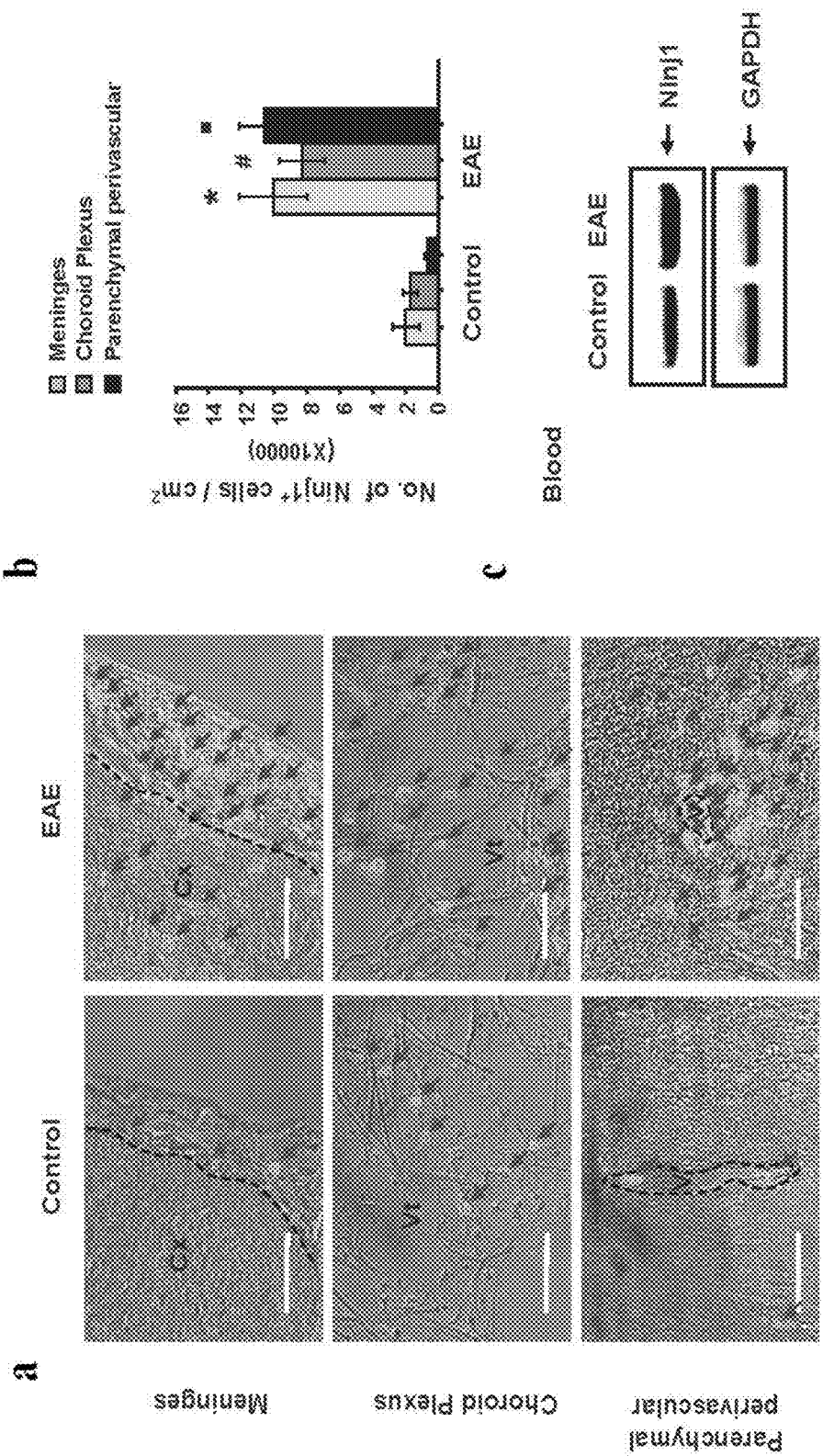
FIG. 22 shows that the number of Ninjurin1 expressing cell is highly abundant in three major compartments such as choroid plexus, meninges, and parenchymal perivascular regions in normal and EAE rats brain (a, b), and Ninjurin1 expression in the blood is increased in EAE rat brain (c).

Ninjurin1 immunostaining results were obtained by three replicates in two control and two EAE animals, and visualized by Axiovert M200 microscopy. Values were converted to fundamental units as Ninjurin1$^+$ cell number per $cm_2$ and graphed as average±standard deviation (FIG. 22B). According to immunostaining of Ninjurin1 in normal and EAE rats brain (FIG. 22), the number of Ninjurin1 expressing cell is highly abundant in three major compartments such as choroid plexus, meninges, and parenchymal perivascular regions. Furthermore, Ninjurin1 expression in the blood is increased in EAE rat brain via RT-PCR.

Experimental Example 10

The Characterization of Ninjurin1 Expressing Cell Type in EAE Rat Brain

To determine the identity of Ninjurin1+ cells in the EAE rat brain, the inventor performed double immunostaining using cell-type specific antibodies. Particularly, Rat brain corresponding a score of 3 were used for double immunostaining through the procedures of experimental example 1 (FIG. 22A) following as bellows cell-type specific markers.

CD11b (Pan macrophage, Abcam)

CD45 (pan leukocyte, Abcam)

Iba-1 (microglia and monocyte, Wako)

MPO-1 (Neutrophil, Dako)

CD4 (T lymphocyte, AbD Setotec)

CD20 (B lymphocyte, Santa cruz)

GFAP (astrocyte, sigma)

GS lectin (macrophage, endothelial cell, molecularprobe)

Ninjurin1 (from Dr. Milbrant)

Figure 23:
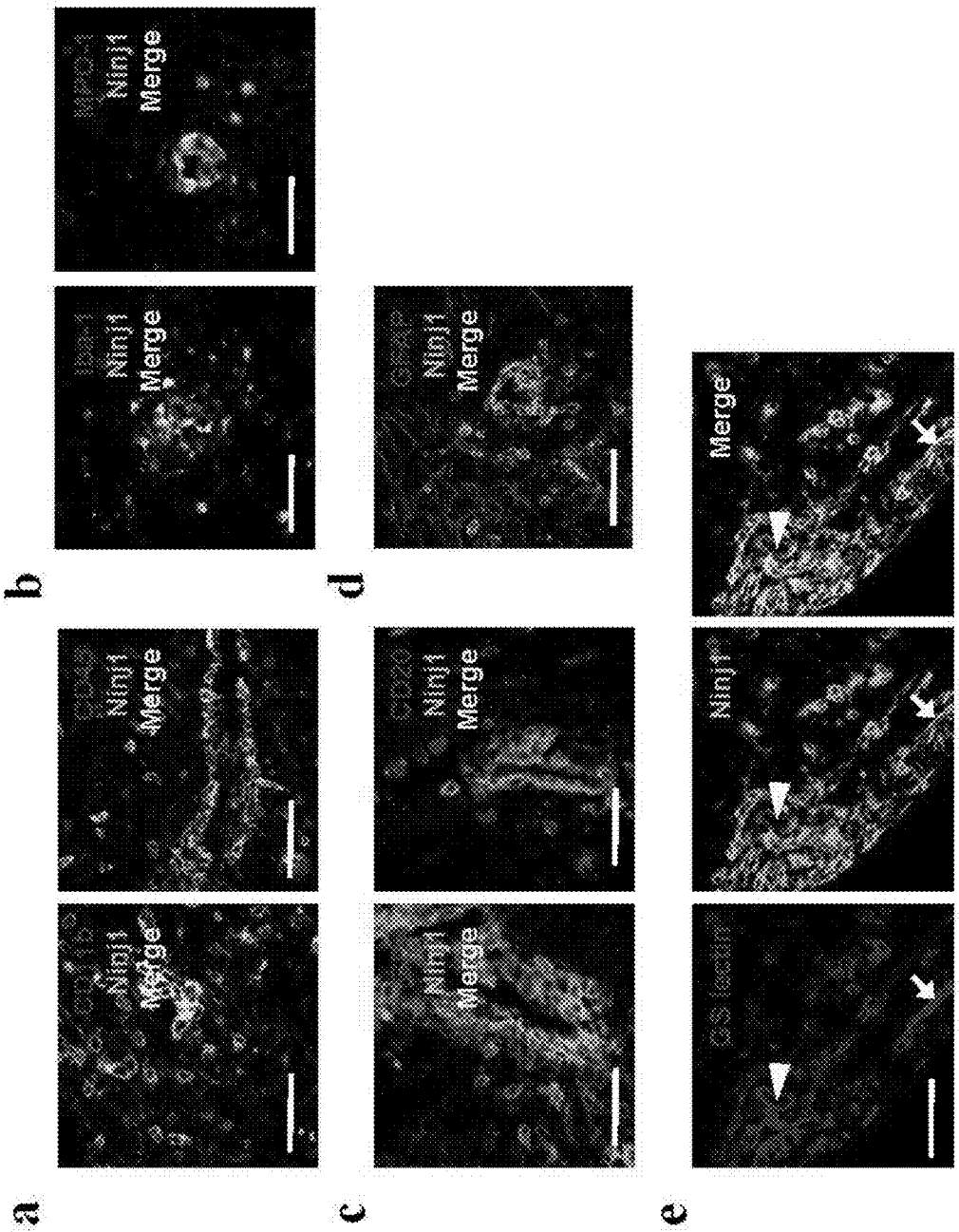
FIG. 23 shows that Ninjurin1-expressing cells were positive for CD11b (an macrophage) and CD45 (pan leukocyte) (a), Iba-1 (microglia and monocyte) and MPO-1 (neutrophil) (b), negative for CD4 (T lymphocyte) and CD20 (B lymphocyte)(c), and GFAP (astrocyte)(d) in EAE rat brain, and Ninjurin1 was partially expressed in some endothelial cells in EAE rat brain (e).

According to FIG. 23, Ninjurin1-expressing cells were positive for CD11b (pan macrophage), CD45 (pan leukocyte, FIG. 23A), Iba-1 (microglia and monocyte, FIG. 23B) and MPO-1 (neutrophil, FIG. 23B), but negative for CD4 (T lymphocyte), CD20 (B lymphocyte, FIG. 23C), and GFAP (astrocyte, FIG. 23D). These results indicate that Ninjurin1 expression is positive in myeloid cells such as macrophages/monocytes and neutrophils, but negative in lymphoid cells such as B lymphocytes and T lymphocytes, as well as for astrocytes.

Furthermore, Some Ninjurin1 signal were merged to GS-lectin which is marker to both macrophage and endothelium. Therefore, Ninjurin1 was partially expressed in some endothelial cells in EAE rat brain (FIG. 23E, arrow) as well as myeloid cells.

Experimental Example 11

The Comparison of Ninjurin1 Expression and Adhesion Activity Against Inflammatory Signals The inventors have thought that Ninjurin1 expresses in myeloid cells within blood and endothelial cells, and promotes the migration of immune cell in tissue. Also, because Ninjurin1-mediated homophilic interaction is well-known, the inventors investigated the adhesion activity by Ninjurin1 between leukocyte and endothelial cell.

Particularly, BV2 cells were grown in Dulbecco's modified Eagle's medium (DMEM) supplemented with 10% fetal bovine serum (FBS, Invitrogen), and HBMECs were grown in M199 medium with 20% FBS, 3 ng/ml bFGF, 1U heparin and maintained in an incubator with a humidified atmosphere of 95% $O_2$ and 5% $CO_2$ at 37° C.

A mouse Ninjurin1 (NM_013610) expression vector was constructed using pCS2+ Myc-tagging plasmid vector. BV2 cells and HBMECs cells were transfected using Lipofectamine Plus reagent (Invitrogen) for Ninjurin1 overexpression. Mock or Ninjurin1 was transfected into BV2 cells and HBMECs and expression was confirmed by Western blot analysis which is performed with specific antibodies including α-tubulin (BioGenex) and c-Myc (Santa Cruz).

For adhesion assay, BV2 cells and HBMECs transfected with pCS2+-Ninjurin1 or pCS2+-Mock (control) DNA were used. For immunocytochemical staining, BV2 cells incubated during 24 hours were labeled with Hoechst (H33342) for 5 min and washed with DMEM. Then, BV2 cells were separated with trypsin/EDTA and detached cells were added to a black flat-bottomed 96 well microtiter plate coated with a monolayer of HBMECs. The plate was incubated for 30 min, washed there times with PBS and the Hoechst positive BV2 cells were counted (FIG. 24C).

For aggregation assay, quantification, BV2 cells and HBMECs transfected with pCS2+–Ninjurin1 or pCS2+– Mock (control) DNA were used. For immunocytochemical staining, BV2 cells incubated during 24 h were labeled with Hoechst (H33342) for 5 min and washed with DMEM. Then, BV2 cells were separated with trypsin/EDTA and detached cells were mixed and incubated for 30 minutes. After visualization by Axoivert M200 microscopy, the numbers of aggregation cell were counted. Each experiment were performed as three independently and demonstrated as average±standard deviation and p-value through student-T test (FIG. 24D).

*, $P<0.01$ versus Mo BV2 cells and Mo HBMECs,
, $P<0.01$ versus Mo BV2 cells and Ninjurin1 HBMECs,
■, $P<0.01$ versus Mo BV2 cells and Mo HBMECs.
Scale bars=50 μm.

Figure 24:
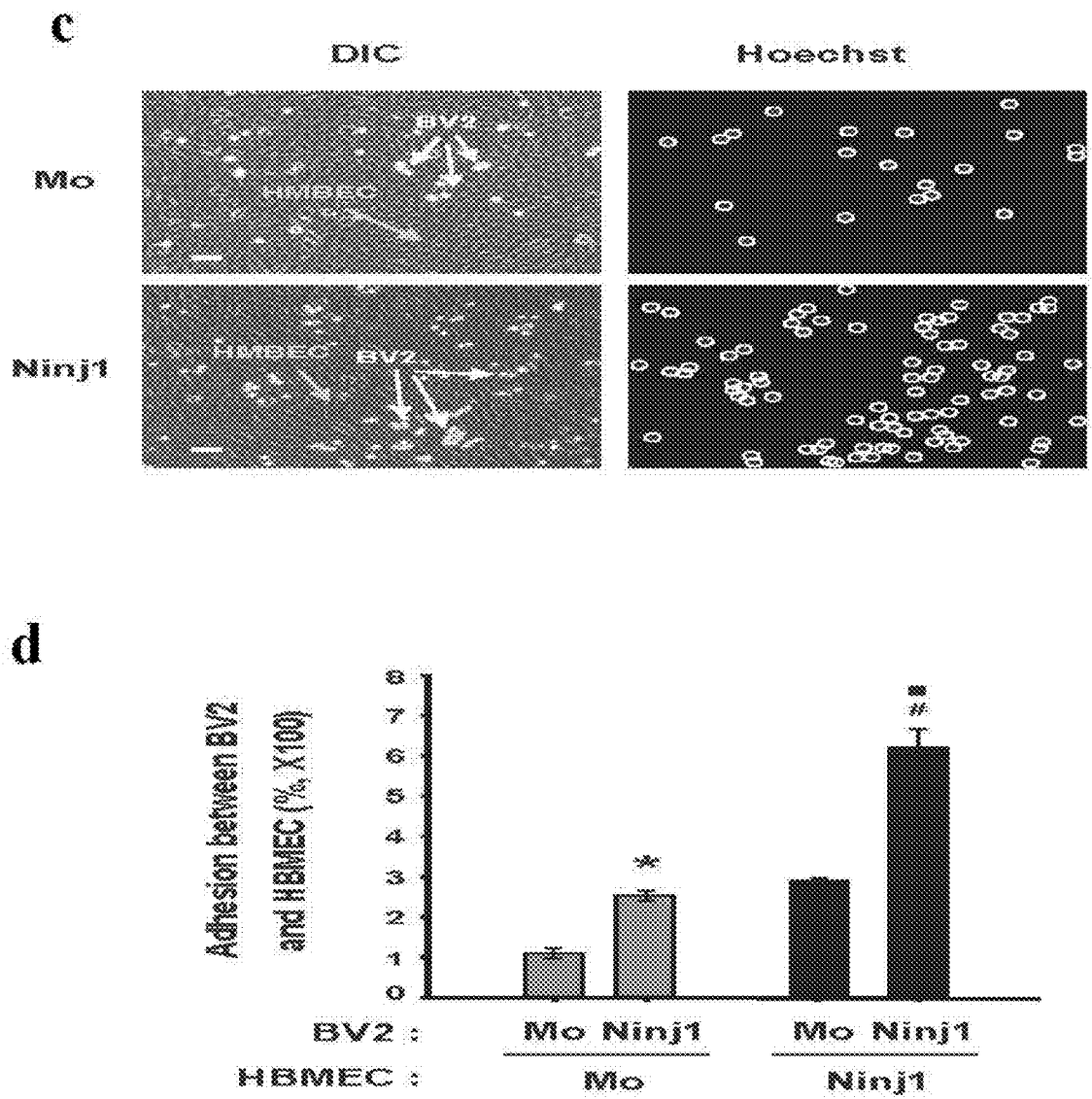
FIG. 24 shows that Ninjurin1 overexpression (a), membrane localization (b) in my-tagging Ninjurin1 transfected BV2 and HBMECs, and overexpressed Ninjurin1 induced adhesion (c), aggregation (d) between BV2 and HBMECs.

According to FIG. 24, inventor confirmed Ninjurin1 overexpression (FIG. 24A) and its membrane localization (FIG. 24B) in my-tagging Ninjurin1 transfected BV2 and HBMECs. Also, overexpressed Ninjurin1 induced adhesion (FIG. 24C) and aggregation (FIG. 24D) between BV2 and HBMECs, that lead to promote leukocyte trafficking via increasing adhesion between leukocyte and endothelial cells in inflammatory conditions.

Experimental Example 12

Design of Inhibitors for Blocking the Ninjurin1-Mediated Adhesion

Figure 25:
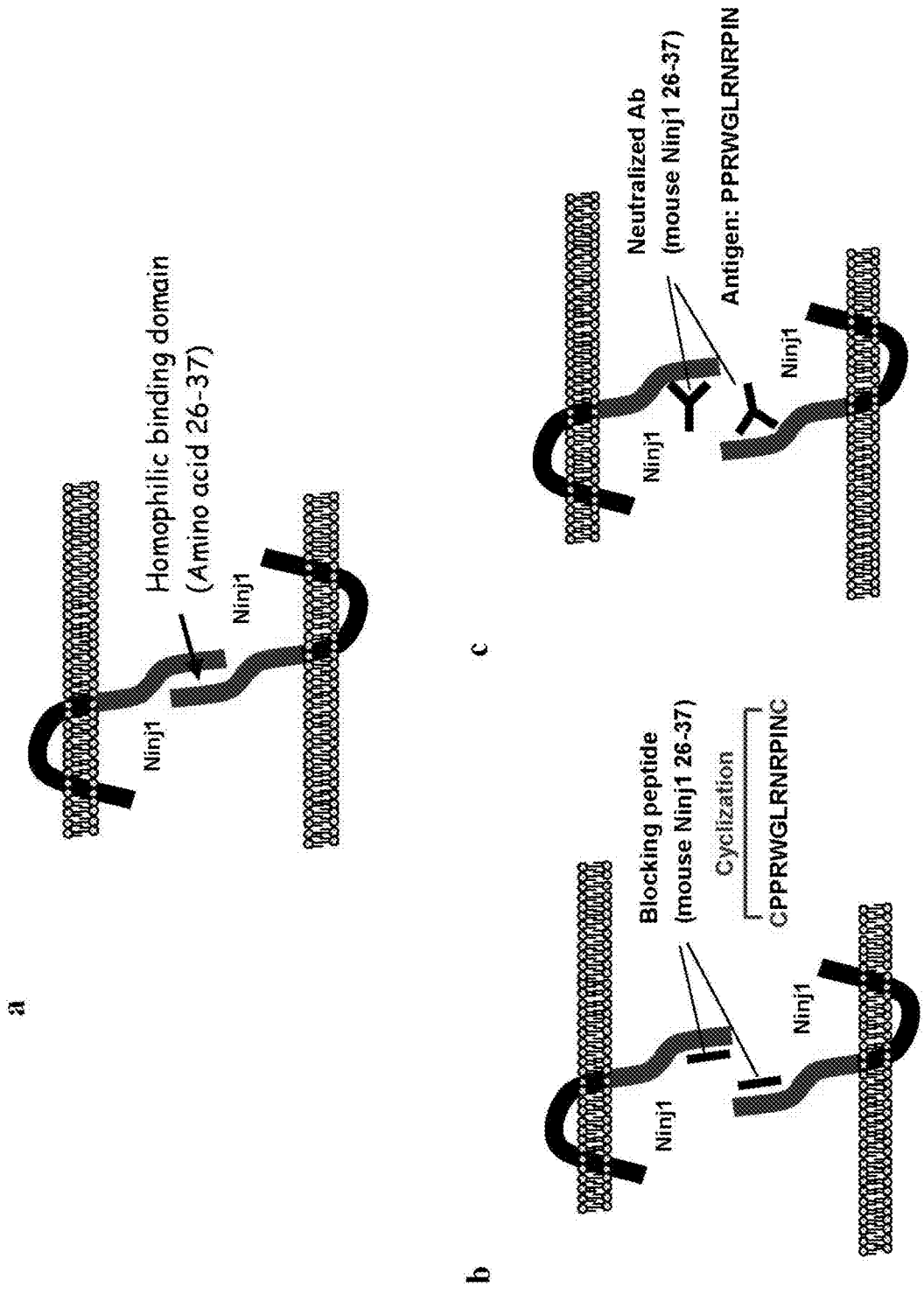
FIG. 25 shows that design of inhibitors for blocking the Ninjurin1-mediated adhesion, Ninjurin1 is known to bind as homophilic manner via its amino acid sequence corresponding from 26 to 37 (AA26-37) (a), blocking cyclic peptide, which is cyclized through cystein residues added in each side of peptide corresponding AA26-37 of Ninjurin1 (b), and neutralizing antibody against antigen corresponding AA26-37 of Ninjurin1 (c).

Because Ninjurin1 is known to bind as homophilic manner via its amino acid sequence corresponding from 26 to 37 (AA26-37) (FIG. 25A), the inventor respected that inhibitor against homophilic binding domain (AA26-37) might modulate inflammatory response. Therefore, the inventor have developed blocking cyclic peptide, which is cyclized through cystein residues added in each side of peptide corresponding AA26-37 of Ninjurin1 (FIG. 25B), as well as neutralizing antibody against antigen corresponding AA26-37 of Ninjurin1 (FIG. 25C).

Experimental Example 13

The Inhibitory Effects of Ninjurin1-Mediated Adhesion by Blocking Peptide and Neutralizing Antibody The inventor investigated the inhibitory effects against homophilic binding activity using cyclic peptide and antibody designed in the experimental example 5. Particularly, Raw264.7 (murine macrophage cell line) and mBEC4 (mouse brain endothelial cell line) were grown in Dulbecco's modified Eagle's medium (DMEM) supplemented with 10% fetal bovine serum (FBS, Invitrogen). Raw264.7 labeled during 5 minutes in 5 μM Carboxyfluorescein diacetate, succinimidyl ester (CSFE, Molecular Probe) incubated during 1 h in media containing cyclic peptide and antibody of each concentrations. Labeled Raw264.7 added in monolayer mBEC4 and incubated during 15 minutes. After 3 times washing by PBS, adhesive Raw264.7 cells were visualized using microscopy (FIG. 26A, C) and analysis the ratio of CSFE positive cells suspended by trypsin/EDTA using FACS (BD). Each experiment was performed as three independent and demonstrated as average±standard error (SEM) and p-value through student-T test (FIG. 26B, D).

*, $P<0.01$, ***, $P<0.001$ (Control versus peptide and antibody)

According to FIG. 26, blocking peptide (FIG. 26A, B) and neutralizing antibody (FIG. 26C, D) significantly reduce Ninjurin1-mediated adhesion activity between leukocyte and endothelial cells.

Experimental Example 14

The Inhibitory Effects of Ninjurin1-Mediated Transmigration by Blocking Peptide and Neutralizing Antibody The inventor investigated the inhibitory effects against trans-migratory activity by cyclic peptide and antibody. Transmigration assay was performed using cells cultured by methods similar to experimental example 6. Particularly, Raw264.7 was incubated and activated via TNFα (10 ng/ml) and INFγ (10 ng/ml) for 12 hours and mBEC4 was activated TNFα (10 ng/ml) and INFγ (10 ng/ml) for 24 hours in upper Transwell (costar). Both Raw264.7 labeled during 5 minutes in 5 uM CSFE and mBEC4 were pre-incubated during 1 hour in media containing cyclic peptide (FIGS. 27A and B) and antibody (FIGS. 27C and D) of each concentration. Labeled Raw264.7 added in monolayer mBEC4 and incubated during 12 hours. After fixation by 4% PFA, upper side of Transwell was cleaned by cotton and sliced and mounted. Migrated cells were visualized using microscopy (FIGS. 27A and C) and analysis the ratio of CSFE labeled cell numbers. Each experiment were performed as three independent and demonstrated as average±standard deviation and p-value through student-T test (FIGS. 27B and D).

*, $P<0.01$, ***, $P<0.001$ (Control versus peptide and antibody)

Figure 27:
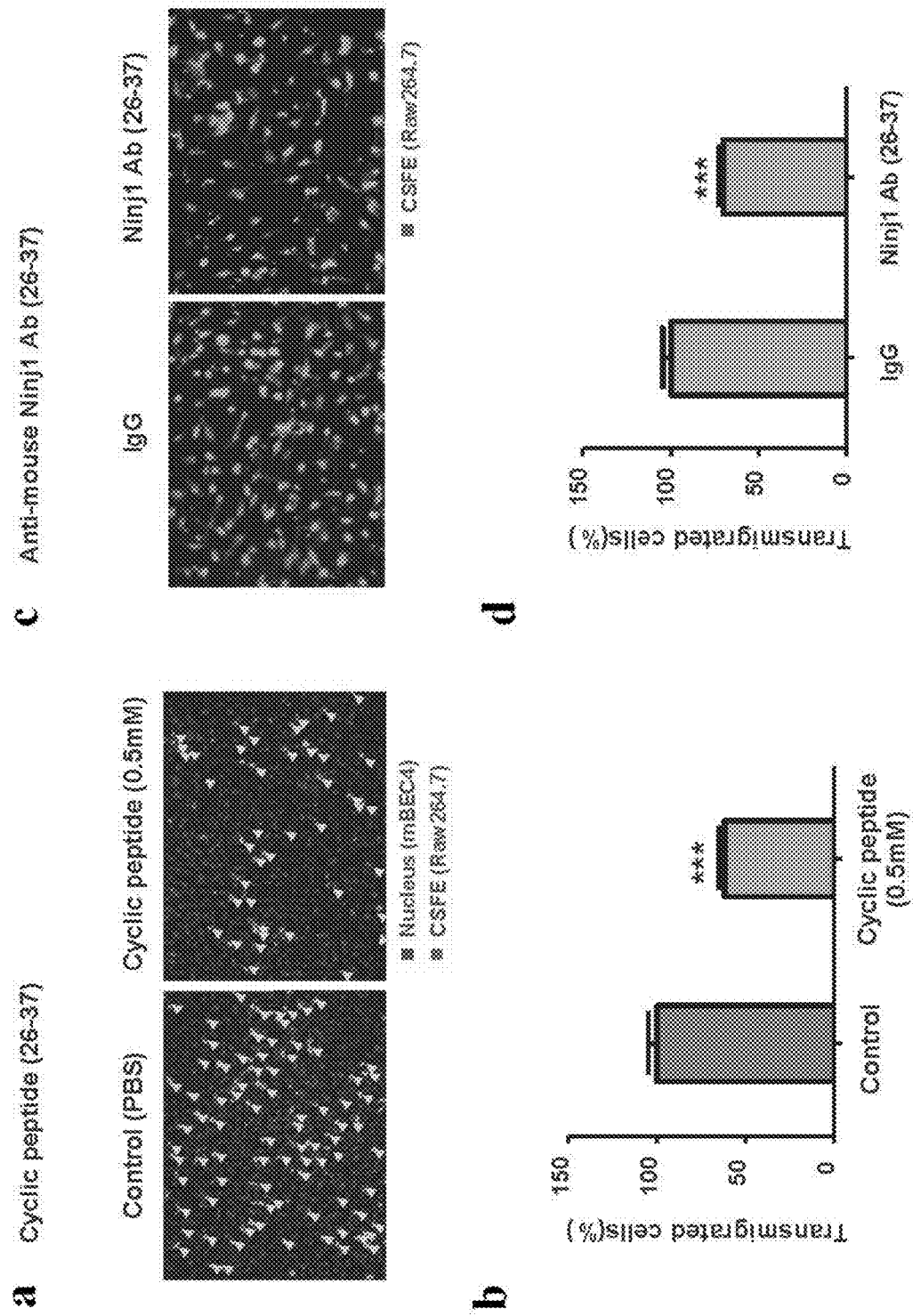
FIG. 27 shows that peptide (a, b) and antibody (c, d) significantly reduced Ninjurin1-mediated transmigration activity of leukocyte across endothelial cells monolayer.

According to FIG. 27, blocking peptide and neutralizing antibody significantly reduce Ninjurin1-mediated transmigration activity of leukocyte across endothelial cells monolayer.

Experimental Example 15

The Protection of EAE by Blocking Peptide

The inventor examined in vivo analysis of Ninjurin1 using experimental autoimmune encephalomyelitis (EAE, animal model of multiple sclerosis), that is mainly caused by infiltration of blood derived immune cells. Animal were maintained under pathogen-free conditions in the animal housing facilities of the College of Pharmacy, Seoul National University for the period of the experiments by the Committee for Care and Use of Laboratory Animals at Seoul National University (SNU-0101011-1).

Particularly, female C57BL/6 weighing 16-20 g and aged 6-10 weeks were immunized subcutaneously with an emulsion containing 100 μg of Myelin Oligodendrocyte Glycoprotein (MOG35-55) in 100 ul of complete Freund's adjuvant (CFA; *Mycobacterium tuberculosis* H37Ra, 4 mg/mL). Each animal was injected with 200 ng of Pertussis Toxin intraperitoneally at 0 day and 3 day after immunization using 3 mice per group. One group was injected 50 μg cyclic peptide at 4, 7, 10, 13, 18 day intraperitoneally and control group was injected PBS. Mice were weighed and observed daily for clinical signs of EAE. The progression of EAE was graded according to the following scale:

1.0: Flaccid tail
1.5: Flaccid tail and impaired right reflex
2.0: Impaired righting reflex and hind limb weakness
2.5: One hind limb paralyzed
3.0: One hind limbs completely paralyzed and another partially paralyzed with residual mobility
4.0: Both hind limbs completely paralyzed
4.5: Both hind limbs completely paralyzed and beginning front limb paralysis Clinical score of each group were demonstrated as average±standard error (SEM) and p-value through student-T test (FIG. 28).

*, $P<0.01$, ***, $P<0.001$ (Control versus peptide treated mice group in each day)

Figure 28:
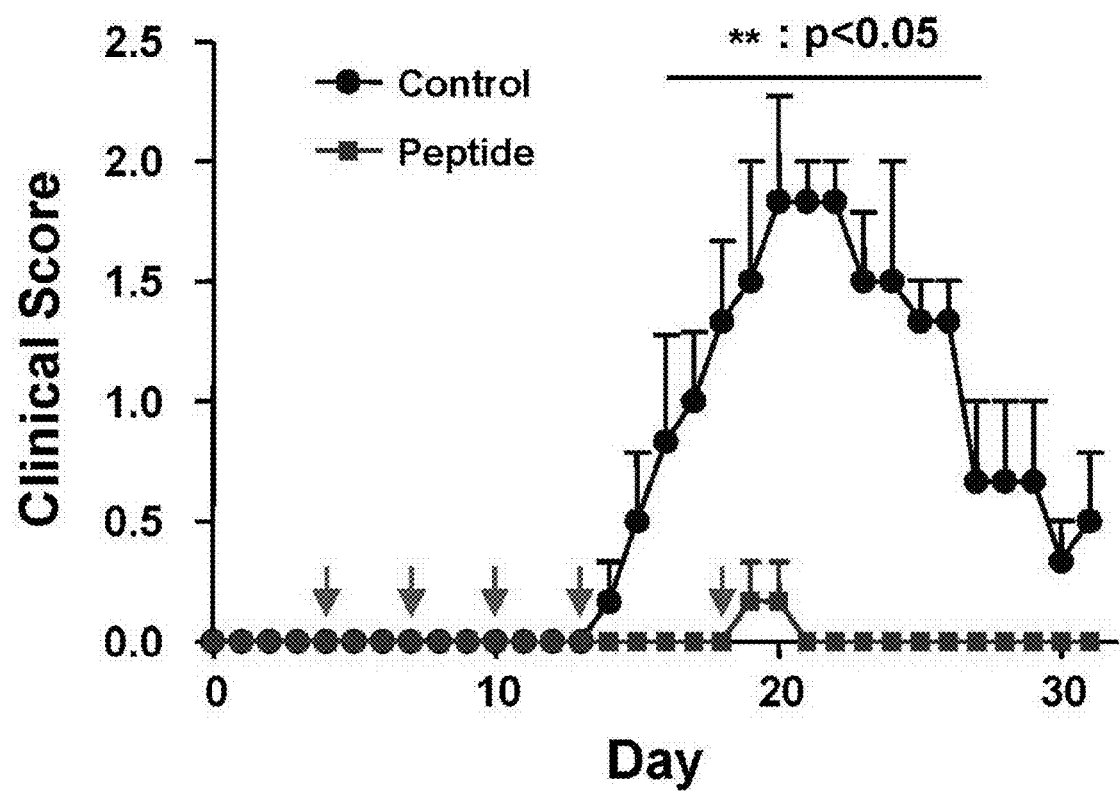
FIG. 28 shows that clinical score of EAE is significantly reduced by cyclic peptide.

According to FIG. 28, Clinical score of EAE is significantly reduced by cyclic peptide. Therefore, cyclic peptide might be attenuated EAE immune response via inhibition of Ninjurin1-mediated interaction between leukocyte and vessel.

Manufacturing Example 1

Preparation of Pharmaceutical Formulations

<1-1> Preparation of Powders

| | |
|---|---|
| *Kluyveromyces* | 2 g |
| Lactose | 1 g |

Powders were prepared by mixing all the above components, which were filled in airtight packs according to the conventional method for preparing powders.

<1-2> Preparation of Tablets

| | |
|---|---|
| *Kluyveromyces* | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| *Kluyveromyces* | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| *Kluyveromyces* | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| *Kluyveromyces* | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Industrial Applicability

The present invention can be effectively applied in the development of drugs for diverse diseases caused by over-activation of macrophages induced by over-expression of Ninjurin1 such as rheumatic arthritis, inflammatory bowel disease, ankylosing spondylitis, psoriasis, atherosclerosis and multiple sclerosis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims

We claim:

1. A method for treating inflammatory disease comprising administering a pharmaceutically effective dose of the composition comprising a Ninjurin 1 protein activation inhibitor to a subject with inflammatory disease, wherein the Ninjurin 1 protein activation inhibitor is selected from the group consisting of a peptide and an antibody,
    wherein the peptide and the antibody complementarily bind to Ninjurin1 protein.

2. The method according to claim 1, wherein the inflammatory disease is selected from the group consisting of rheumatic arthritis, inflammatory bowel disease, ankylosing spondylitis, psoriasis, atherosclerosis and multiple sclerosis.

3. The method according to claim 1, wherein the Ninjurinl protein has the amino acid sequence represented by SEQ. ID. NO: 1.

* * * * *

SEQUENCE LISTING

<160> NUMBER OF SEQ ID NOS: 19

<210> SEQ ID NO 1

-continued

```
<211> LENGTH: 152
<212> TYPE: PRT
<213> ORGANISM: Homo sapiens

<400> SEQUENCE: 1

Met Asp Ser Gly Thr Glu Glu Tyr Glu Leu Asn Gly Gly Leu Pro Pro
1               5                   10                  15

Gly Thr Pro Gly Ser Pro Asp Ala Ser Pro Ala Arg Trp Gly Trp Arg
            20                  25                  30

His Gly Pro Ile Asn Val Asn His Tyr Ala Ser Lys Ser Ala Ala
        35                  40                  45

Glu Ser Met Leu Asp Ile Ala Leu Leu Met Ala Asn Ala Ser Gln Leu
    50                  55                  60

Lys Ala Val Val Glu Gln Gly Pro Ser Phe Ala Phe Tyr Val Pro Leu
65                  70                  75                  80

Val Val Leu Ile Ser Ile Ser Leu Val Leu Gln Ile Gly Val Gly Val
                85                  90                  95

Leu Leu Ile Phe Leu Val Lys Tyr Asp Leu Asn Asn Pro Asp Lys His
            100                 105                 110

Ala Lys Leu Asp Phe Leu Asn Asn Leu Ala Thr Gly Leu Val Phe Ile
        115                 120                 125

Ile Val Val Asn Ile Phe Ile Thr Ala Phe Gly Val Gln Lys Pro
    130                 135                 140

Leu Met Asp Met Ala Pro Gln Gln
145                 150

<210> SEQ ID NO 2
<211> LENGTH: 29
<212> TYPE: DNA
<213> ORGANISM: Artificial Sequence
<220> FEATURE:
<223> OTHER INFORMATION: primer 1 of mouse Ninjurin1 cDNA

<400> SEQUENCE: 2
gggaattcca tggagtcggg cactgagga                                    29

<210> SEQ ID NO 3
<211> LENGTH: 31
<212> TYPE: DNA
<213> ORGANISM: Artificial Sequence
<220> FEATURE:
<223> OTHER INFORMATION: primer 2 of mouse Ninjurin1 cDNA

<400> SEQUENCE: 3
ctcctcgagt tctactgccg gggcgccacg t                                 31

<210> SEQ ID NO 4
<211> LENGTH: 20
<212> TYPE: DNA
<213> ORGANISM: Artificial Sequence
<220> FEATURE:
<223> OTHER INFORMATION: forward primer of Gapdh

<400> SEQUENCE: 4
accacagtcc atgccatcac                                              20

<210> SEQ ID NO 5
<211> LENGTH: 20
<212> TYPE: DNA
<213> ORGANISM: Artificial Sequence
<220> FEATURE:
<223> OTHER INFORMATION: reverse primer of Gapdh
```

<400> SEQUENCE: 5
tccaccaccc tgttgctgta                                                    20

<210> SEQ ID NO 6
<211> LENGTH: 17
<212> TYPE: DNA
<213> ORGANISM: Artificial Sequence
<220> FEATURE:
<223> OTHER INFORMATION: forward primer of Ninjurin1

<400> SEQUENCE: 6
gagtcgggca ctgagga                                                       17

<210> SEQ ID NO 7
<211> LENGTH: 18
<212> TYPE: DNA
<213> ORGANISM: Artificial Sequence
<220> FEATURE:
<223> OTHER INFORMATION: reverse primer of Ninjurin1

<400> SEQUENCE: 7
gttgcagggg tctggtca                                                      18

<210> SEQ ID NO 8
<211> LENGTH: 20
<212> TYPE: DNA
<213> ORGANISM: Artificial Sequence
<220> FEATURE:
<223> OTHER INFORMATION: forward primer of Ang1

<400> SEQUENCE: 8
aggcttggtt tctcgtcaga                                                    20

<210> SEQ ID NO 9
<211> LENGTH: 20
<212> TYPE: DNA
<213> ORGANISM: Artificial Sequence
<220> FEATURE:
<223> OTHER INFORMATION: reverse primer of Ang1

<400> SEQUENCE: 9
tctgcacagt ctcgaaatgg                                                    20

<210> SEQ ID NO 10
<211> LENGTH: 23
<212> TYPE: DNA
<213> ORGANISM: Artificial Sequence
<220> FEATURE:
<223> OTHER INFORMATION: forward primer of Ang2

<400> SEQUENCE: 10
gctgctggtt tattactgaa gaa                                                23

<210> SEQ ID NO 11
<211> LENGTH: 22
<212> TYPE: DNA
<213> ORGANISM: Artificial Sequence
<220> FEATURE:
<223> OTHER INFORMATION: reverse primer of Ang2

<400> SEQUENCE: 11
tcaggtggac tgggatgttt ag                                                 22

<210> SEQ ID NO 12

```
<211> LENGTH: 22
<212> TYPE: DNA
<213> ORGANISM: Artificial Sequence
<220> FEATURE:
<223> OTHER INFORMATION: forward primer of Wnt7b

<400> SEQUENCE: 12
aagaactccg agtagggagt cg                                                  22

<210> SEQ ID NO 13
<211> LENGTH: 22
<212> TYPE: DNA
<213> ORGANISM: Artificial Sequence
<220> FEATURE:
<223> OTHER INFORMATION: reverse primer of Wnt7b

<400> SEQUENCE: 13
tgcgttgtac ttctccttga gc                                                  22

<210> SEQ ID NO 14
<211> LENGTH: 20
<212> TYPE: DNA
<213> ORGANISM: Artificial Sequence
<220> FEATURE:
<223> OTHER INFORMATION: forward primer of Wnt7b 2nd round

<400> SEQUENCE: 14
ccgagtaggg agtcgagagg                                                     20

<210> SEQ ID NO 15
<211> LENGTH: 22
<212> TYPE: DNA
<213> ORGANISM: Artificial Sequence
<220> FEATURE:
<223> OTHER INFORMATION: reverse primer of Wnt7b 2nd round

<400> SEQUENCE: 15
cacaccgtga cacttacatt cc                                                  22

<210> SEQ ID NO 16
<211> LENGTH: 20
<212> TYPE: DNA
<213> ORGANISM: Artificial Sequence
<220> FEATURE:
<223> OTHER INFORMATION: forward primer of Ang2

<400> SEQUENCE: 16
tgtgatcttg tcttggccgc                                                     20

<210> SEQ ID NO 17
<211> LENGTH: 21
<212> TYPE: DNA
<213> ORGANISM: Artificial Sequence
<220> FEATURE:
<223> OTHER INFORMATION: reverse primer of Ang2

<400> SEQUENCE: 17
agagggagtg ttccaagaag c                                                   21

<210> SEQ ID NO 18
<211> LENGTH: 18
<212> TYPE: DNA
<213> ORGANISM: Artificial Sequence
<220> FEATURE:
<223> OTHER INFORMATION: forward primer of Ninjurin1-sense

<400> SEQUENCE: 18
```

```
catctctctc gtgctgca                                           18

<210> SEQ ID NO 19
<211> LENGTH: 18
<212> TYPE: DNA
<213> ORGANISM: Artificial Sequence
<220> FEATURE:
<223> OTHER INFORMATION: reverse primer of Ninjurin1-antisense

<400> SEQUENCE: 19
gccaagagac actgccaa                                           18
```